US010192024B2

(12) United States Patent
Chen et al.

(10) Patent No.: US 10,192,024 B2
(45) Date of Patent: Jan. 29, 2019

(54) SYSTEM AND METHOD FOR GENERATION AND USE OF OPTIMAL NUCLEOTIDE FLOW ORDERS

(71) Applicant: 454 Life Sciences Corporation, Branford, CT (US)

(72) Inventors: Yi-Ju Chen, New Haven, CT (US); Chiu Tai Andrew Wong, Northford, CT (US)

(73) Assignee: 454 Life Sciences Corporation, Branford, CT (US)

( * ) Notice: Subject to any disclaimer, the term of this patent is extended or adjusted under 35 U.S.C. 154(b) by 1227 days.

(21) Appl. No.: 13/801,867

(22) Filed: Mar. 13, 2013

(65) Prior Publication Data
US 2013/0311105 A1 Nov. 21, 2013

Related U.S. Application Data

(60) Provisional application No. 61/648,783, filed on May 18, 2012.

(51) Int. Cl.
| G01N 33/50 | (2006.01) |
| G06F 19/12 | (2011.01) |
| G06F 19/20 | (2011.01) |
| G06F 19/22 | (2011.01) |
| G06F 19/24 | (2011.01) |

(52) U.S. Cl.
CPC .............. G06F 19/12 (2013.01); G06F 19/20 (2013.01); G06F 19/22 (2013.01); G06F 19/24 (2013.01)

(58) Field of Classification Search
None
See application file for complete search history.

(56) References Cited

U.S. PATENT DOCUMENTS

| 6,210,891 | B1 | 4/2001 | Nyren et al. |
| 6,258,568 | B1 | 7/2001 | Nyren |
| 6,274,320 | B1 | 8/2001 | Rothberg et al. |
| 6,828,100 | B1 | 12/2004 | Ronaghi |
| 6,952,651 | B2 | 10/2005 | Su |
| 7,211,390 | B2 | 5/2007 | Rothberg et al. |
| 7,244,559 | B2 | 7/2007 | Rothberg et al. |
| 7,264,929 | B2 | 9/2007 | Rothberg et al. |
| 7,323,305 | B2 | 1/2008 | Leamon et al. |
| 7,335,762 | B2 | 2/2008 | Rothberg et al. |
| 7,575,865 | B2 | 8/2009 | Leamon et al. |
| 7,601,499 | B2 | 10/2009 | Berka et al. |
| 7,622,280 | B2 | 11/2009 | Holliger et al. |
| 7,638,276 | B2 | 12/2009 | Griffiths et al. |
| 7,682,816 | B2 | 3/2010 | Kim et al. |
| 7,842,457 | B2 | 11/2010 | Berka et al. |
| 7,888,034 | B2 | 2/2011 | Simen et al. |
| 7,927,797 | B2 | 4/2011 | Nobile et al. |
| 8,012,690 | B2 | 9/2011 | Berka et al. |
| 8,301,394 | B2 | 10/2012 | Chen et al. |
| 8,364,417 | B2 | 1/2013 | Chen et al. |
| 8,748,102 | B2 | 6/2014 | Berka et al. |
| 2004/0185484 | A1 | 9/2004 | Costa et al. |
| 2006/0228721 | A1 | 10/2006 | Leamon et al. |
| 2008/0003424 | A1 | 1/2008 | Kawamura |
| 2009/0053724 | A1 | 2/2009 | Roth et al. |
| 2009/0105959 | A1 | 4/2009 | Braverman et al. |
| 2009/0203086 | A1 | 8/2009 | Chen et al. |
| 2009/0233291 | A1 | 9/2009 | Chen et al. |
| 2010/0136516 | A1 | 6/2010 | Simen et al. |
| 2011/0003701 | A1 | 1/2011 | Ferreri et al. |
| 2011/0177587 | A1 | 7/2011 | Nobile et al. |
| 2011/0201526 | A1 | 8/2011 | Berka et al. |
| 2013/0288904 | A1* | 10/2013 | Hubbell ............... C12Q 1/6874 506/2 |

FOREIGN PATENT DOCUMENTS

| CN | 1662662 | 8/2005 |
| WO | WO-05040425 A2 | 5/2005 |
| WO | WO-07098049 A2 | 8/2007 |
| WO | WO-08115427 A2 | 9/2008 |

OTHER PUBLICATIONS

DeAngelis et al. "Solid-Phase Reversible Immobilization for the Isolation of PCR Products." *Nucleic Acids Res.* 23.22(1995):4742-4743.
Merrifield. "Solid-Phase Peptide Synthesis. III. An Improved Synthesis of Bradykinin." *Biochem.* 3.9(1964):1385-1390.
Ronaghi. "Pyrosequencing Sheds Light on DNA Sequencing." *Genome Res.* 11(2001):3-11.
Invitation to Pay Additional Fees and, Where Applicable, Protest Fee issued in International Application No. PCT/EP2013/060152 dated Jan. 9, 2014.
DeAngelis, M. et al. "Solid-Phase Reversible Immobilization for the Isolation of PCR Products" *Nucleic Acids Research*, 1995, vol. 23, No. 22, p. 4742-4743.
Margulies M. et al. "Genome sequencing in microfabricated high-density picolitre reactors", Nature, 2005, vol. 437, p. 376-380.
Merrifield, "Solid-Phase Peptide Synthesis", *Biochemistry*, 1964, vol. 3, No. 9, p. 1385-1390.
Ronaghi, M. "Pyrosequencing sheds light on DNA sequencing", Genome Research, 2001, vol. 11, p. 3-11.

* cited by examiner

*Primary Examiner* — Jason M Sims
(74) *Attorney, Agent, or Firm* — Cooley LLP; Ivor R. Elrifi; Christina K. Stock

(57) ABSTRACT

An embodiment of a method for generating a flow order that minimizes the accumulation of phasic synchrony error in sequence data is described that comprises the steps of: (a) generating a plurality of sequential orderings of nucleotides species comprising a k-base length, wherein the sequential orderings define a sequence of introduction of nucleotide species into a sequencing by synthesis reaction environment; (b) simulating acquisition of sequence data from one or more reference genomes using the sequential orderings, wherein the sequence data comprises an accumulation of phasic synchrony error; and (c) selecting one or more of the sequential orderings using a read length parameter and an extension rate parameter.

7 Claims, 4 Drawing Sheets
Specification includes a Sequence Listing.

SEQUENCE LISTING

```
<160> NUMBER OF SEQ ID NOS: 147

<210> SEQ ID NO 1
<211> LENGTH: 12
<212> TYPE: DNA
<213> ORGANISM: Artificial Sequence
<220> FEATURE:
<223> OTHER INFORMATION: A 12-base flow order.

<400> SEQUENCE: 1
tcgtgacgtc ta                                                          12

<210> SEQ ID NO 2
<211> LENGTH: 32
<212> TYPE: DNA
<213> ORGANISM: Artificial Sequence
<220> FEATURE:
<223> OTHER INFORMATION: An example of an effective flow order.

<400> SEQUENCE: 2
tacgtctgag catcgatcga tgtacagcta cg                                    32

<210> SEQ ID NO 3
<211> LENGTH: 24
<212> TYPE: DNA
<213> ORGANISM: Artificial Sequence
<220> FEATURE:
<223> OTHER INFORMATION: An example of an effective flow order.

<400> SEQUENCE: 3
agcgtactgc atgcatcagt atgc                                             24

<210> SEQ ID NO 4
<211> LENGTH: 32
<212> TYPE: DNA
<213> ORGANISM: Artificial Sequence
<220> FEATURE:
<223> OTHER INFORMATION: An example of an effective flow order.

<400> SEQUENCE: 4
catatgcatg atcagctcga tgacgcatgc tg                                    32

<210> SEQ ID NO 5
<211> LENGTH: 32
<212> TYPE: DNA
<213> ORGANISM: Artificial Sequence
<220> FEATURE:
<223> OTHER INFORMATION: An example of an effective flow order.

<400> SEQUENCE: 5
tgctcgatga tgtcatcgac tgactgacag ca                                    32

<210> SEQ ID NO 6
<211> LENGTH: 32
<212> TYPE: DNA
<213> ORGANISM: Artificial Sequence
<220> FEATURE:
<223> OTHER INFORMATION: An example of an effective flow order.

<400> SEQUENCE: 6
acagcgtgat actgtcgatg actgcatcat cg                                    32

<210> SEQ ID NO 7
<211> LENGTH: 32
<212> TYPE: DNA
<213> ORGANISM: Artificial Sequence
```

```
<220> FEATURE:
<223> OTHER INFORMATION: An example of an effective flow order.

<400> SEQUENCE: 7
acgtgtacga cgtatcacgt atgcactgag tc                                   32

<210> SEQ ID NO 8
<211> LENGTH: 32
<212> TYPE: DNA
<213> ORGANISM: Artificial Sequence
<220> FEATURE:
<223> OTHER INFORMATION: An example of an effective flow order.

<400> SEQUENCE: 8
acagtctcga tgacagtata cgtctgcgat gc                                   32

<210> SEQ ID NO 9
<211> LENGTH: 32
<212> TYPE: DNA
<213> ORGANISM: Artificial Sequence
<220> FEATURE:
<223> OTHER INFORMATION: An example of an effective flow order.

<400> SEQUENCE: 9
tgctacatga tgacgcagac tgtcatagct cg                                   32

<210> SEQ ID NO 10
<211> LENGTH: 12
<212> TYPE: DNA
<213> ORGANISM: Artificial Sequence
<220> FEATURE:
<223> OTHER INFORMATION: An exemplary Flow Order A

<400> SEQUENCE: 10
tacgtacgta cg                                                         12

<210> SEQ ID NO 11
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 11
agcgtactgc atgcatcagt atgcg                                           25

<210> SEQ ID NO 12
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 12
agcgtactgc atgcatcagt atgct                                           25

<210> SEQ ID NO 13
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 13
agcgtactgc atgcatcagt atcgc                                           25
```

<210> SEQ ID NO 14
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 14
agcgtactgc atgcatcagt atgac                                        25

<210> SEQ ID NO 15
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 15
agcgtactgc atgcatcagt atcgc                                        25

<210> SEQ ID NO 16
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 16
agcgtactgc atgcatcagt atgct                                        25

<210> SEQ ID NO 17
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 17
agcgtactgc atgcatcagt atgcg                                        25

<210> SEQ ID NO 18
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 18
agcgtactgc atgcatcagt atgac                                        25

<210> SEQ ID NO 19
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 19
agcgtactgc atgcatcagt atcgc                                        25

<210> SEQ ID NO 20
<211> LENGTH: 25
<212> TYPE: DNA
<213> ORGANISM: Artificial Sequence
<220> FEATURE:
<223> OTHER INFORMATION: An exemplary Flow Order A

```
<400> SEQUENCE: 20
agcgtactgc atgcatcagt atgct                                                 25

<210> SEQ ID NO 21
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 21
agcgtactgc atgcatcagt atgcg                                                 25

<210> SEQ ID NO 22
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 22
agcgtactgc atgcatcagt atgac                                                 25

<210> SEQ ID NO 23
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 23
agcgtactgc atgcatcagt atgcg                                                 25

<210> SEQ ID NO 24
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 24
agcgtactgc atgcatcagt atgct                                                 25

<210> SEQ ID NO 25
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 25
agcgtactgc atgcatcagt atcgc                                                 25

<210> SEQ ID NO 26
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 26
agcgtactgc atgcatcagt atgac                                                 25

<210> SEQ ID NO 27
```

<210> SEQ ID NO 27
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 27
agcgtactgc atgcatcagt atgcg                                    25

<210> SEQ ID NO 28
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 28
agcgtactgc atgcatcagt atcgc                                    25

<210> SEQ ID NO 29
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 29
agcgtactgc atgcatcagt atgct                                    25

<210> SEQ ID NO 30
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 30
agcgtactgc atgcatcagt atgac                                    25

<210> SEQ ID NO 31
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 31
agcgtactgc atgcatcagt atgct                                    25

<210> SEQ ID NO 32
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 32
agcgtactgc atgcatcagt atcgc                                    25

<210> SEQ ID NO 33
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 33
agcgtactgc atgcatcagt atgcg                                              25

<210> SEQ ID NO 34
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 34
agcgtactgc atgcatcagt atgac                                              25

<210> SEQ ID NO 35
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 35
agcgtactgc atgcatcagt atcgc                                              25

<210> SEQ ID NO 36
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 36
agcgtactgc atgcatcagt atgcg                                              25

<210> SEQ ID NO 37
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 37
agcgtactgc atgcatcagt atgac                                              25

<210> SEQ ID NO 38
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 38
agcgtactgc atgcatcagt atgct                                              25

<210> SEQ ID NO 39
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 39
agcgtactgc atgcatcagt atgcg                                              25

<210> SEQ ID NO 40
<211> LENGTH: 25
<212> TYPE: DNA

```
<213> ORGANISM: Artificial Sequence
<220> FEATURE:
<223> OTHER INFORMATION: An exemplary Flow Order A

<400> SEQUENCE: 40
agcgtactgc atgcatcagt atcgc                                              25

<210> SEQ ID NO 41
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 41
agcgtactgc atgcatcagt atgac                                              25

<210> SEQ ID NO 42
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 42
agcgtactgc atgcatcagt atgct                                              25

<210> SEQ ID NO 43
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 43
agcgtactgc atgcatcagt atgcg                                              25

<210> SEQ ID NO 44
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 44
agcgtactgc atgcatcagt atgct                                              25

<210> SEQ ID NO 45
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 45
agcgtactgc atgcatcagt atgac                                              25

<210> SEQ ID NO 46
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 46
agcgtactgc atgcatcagt atcgc                                              25
```

<210> SEQ ID NO 47
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 47
agcgtactgc atgcatcagt atgac                                  25

<210> SEQ ID NO 48
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 48
agcgtactgc atgcatcagt atcgc                                  25

<210> SEQ ID NO 49
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 49
agcgtactgc atgcatcagt atgcg                                  25

<210> SEQ ID NO 50
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 50
agcgtactgc atgcatcagt atgct                                  25

<210> SEQ ID NO 51
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 51
agcgtactgc atgcatcagt atgcg                                  25

<210> SEQ ID NO 52
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 52
agcgtactgc atgcatcagt atgct                                  25

<210> SEQ ID NO 53
<211> LENGTH: 25
<212> TYPE: DNA
<213> ORGANISM: Artificial Sequence
<220> FEATURE:

<223> OTHER INFORMATION: An exemplary Flow Order A

<400> SEQUENCE: 53
agcgtactgc atgcatcagt atgac                                    25

<210> SEQ ID NO 54
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 54
agcgtactgc atgcatcagt atcgc                                    25

<210> SEQ ID NO 55
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 55
agcgtactgc atgcatcagt atgct                                    25

<210> SEQ ID NO 56
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 56
agcgtactgc atgcatcagt atgcg                                    25

<210> SEQ ID NO 57
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 57
agcgtactgc atgcatcagt atgac                                    25

<210> SEQ ID NO 58
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 58
agcgtactgc atgcatcagt atcgc                                    25

<210> SEQ ID NO 59
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 59
agcgtactgc atgcatcagt atgac                                    25

```
<210> SEQ ID NO 60
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 60
agcgtactgc atgcatcagt atgcg                                    25

<210> SEQ ID NO 61
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 61
agcgtactgc atgcatcagt atcgc                                    25

<210> SEQ ID NO 62
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 62
agcgtactgc atgcatcagt atgct                                    25

<210> SEQ ID NO 63
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 63
agcgtactgc atgcatcagt atgcg                                    25

<210> SEQ ID NO 64
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 64
agcgtactgc atgcatcagt atgac                                    25

<210> SEQ ID NO 65
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 65
agcgtactgc atgcatcagt atcgc                                    25

<210> SEQ ID NO 66
<211> LENGTH: 25
<212> TYPE: DNA
<213> ORGANISM: Artificial Sequence
<220> FEATURE:
<223> OTHER INFORMATION: An exemplary Flow Order A
```

<400> SEQUENCE: 66
agcgtactgc atgcatcagt atgct       25

<210> SEQ ID NO 67
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 67
agcgtactgc atgcatcagt atgac       25

<210> SEQ ID NO 68
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 68
agcgtactgc atgcatcagt atgct       25

<210> SEQ ID NO 69
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 69
agcgtactgc atgcatcagt atcgc       25

<210> SEQ ID NO 70
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 70
agcgtactgc atgcatcagt atgcg       25

<210> SEQ ID NO 71
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 71
agcgtactgc atgcatcagt atgct       25

<210> SEQ ID NO 72
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 72
agcgtactgc atgcatcagt atcgc       25

<210> SEQ ID NO 73
<211> LENGTH: 25

```
<212> TYPE: DNA
<213> ORGANISM: Artificial Sequence
<220> FEATURE:
<223> OTHER INFORMATION: An exemplary Flow Order A

<400> SEQUENCE: 73
agcgtactgc atgcatcagt atgcg                                              25

<210> SEQ ID NO 74
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 74
agcgtactgc atgcatcagt atgac                                              25

<210> SEQ ID NO 75
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 75
agcgtactgc atgcatcagt atgcg                                              25

<210> SEQ ID NO 76
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 76
agcgtactgc atgcatcagt atgac                                              25

<210> SEQ ID NO 77
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 77
agcgtactgc atgcatcagt atcgc                                              25

<210> SEQ ID NO 78
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 78
agcgtactgc atgcatcagt atgct                                              25

<210> SEQ ID NO 79
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 79
```
agcgtactgc atgcatcagt atgac                                            25

<210> SEQ ID NO 80
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 80
agcgtactgc atgcatcagt atgcg                                            25

<210> SEQ ID NO 81
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 81
agcgtactgc atgcatcagt atcgc                                            25

<210> SEQ ID NO 82
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 82
agcgtactgc atgcatcagt atgct                                            25

<210> SEQ ID NO 83
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 83
agcgtactgc atgcatcagt atgcg                                            25

<210> SEQ ID NO 84
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 84
agcgtactgc atgcatcagt atgct                                            25

<210> SEQ ID NO 85
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 85
agcgtactgc atgcatcagt atgac                                            25

<210> SEQ ID NO 86
<211> LENGTH: 25
<212> TYPE: DNA
<213> ORGANISM: Artificial Sequence

```
<220> FEATURE:
<223> OTHER INFORMATION: An exemplary Flow Order A

<400> SEQUENCE: 86
agcgtactgc atgcatcagt atcgc                                          25

<210> SEQ ID NO 87
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 87
agcgtactgc atgcatcagt atgct                                          25

<210> SEQ ID NO 88
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 88
agcgtactgc atgcatcagt atgac                                          25

<210> SEQ ID NO 89
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 89
agcgtactgc atgcatcagt atgcg                                          25

<210> SEQ ID NO 90
<211> LENGTH: 25
<212> TYPE: DNA
<213> ORGANISM: Artificial Sequence
<220> FEATURE:
<223> OTHER INFORMATION: An exemplary Flow Order A

<400> SEQUENCE: 90
agcgtactgc atgcatcagt atcgc                                          25

<210> SEQ ID NO 91
<211> LENGTH: 12
<212> TYPE: DNA
<213> ORGANISM: Artificial Sequence
<220> FEATURE:
<223> OTHER INFORMATION: An exemplary Flow Order B

<400> SEQUENCE: 91
tacgtacgta cg                                                        12

<210> SEQ ID NO 92
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 92
atgtagtcga gcatcatctg acgcagtacg tgc                                 33
```

```
<210> SEQ ID NO 93
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 93
atgatctcag tcagcagcta tgtcagtgca tgc                                33

<210> SEQ ID NO 94
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 94
agtgactgat cgtcatcagc tagcatcgac tgc                                33

<210> SEQ ID NO 95
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 95
atagatcgca tgacgatcgc atatcgtcag tgc                                33

<210> SEQ ID NO 96
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 96
atgtagtcga gcatcatctg acgcagtacg tgc                                33

<210> SEQ ID NO 97
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 97
atgatctcag tcagcagcta tgtcagtgca tgc                                33

<210> SEQ ID NO 98
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 98
atagatcgca tgacgatcgc atatcgtcag tgc                                33

<210> SEQ ID NO 99
<211> LENGTH: 33
<212> TYPE: DNA
<213> ORGANISM: Artificial Sequence
<220> FEATURE:
<223> OTHER INFORMATION: An exemplary Flow Order B
```

```
<400> SEQUENCE: 99
agtgactgat cgtcatcagc tagcatcgac tgc                            33

<210> SEQ ID NO 100
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 100
atgtagtcga gcatcatctg acgcagtacg tgc                            33

<210> SEQ ID NO 101
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 101
atagatcgca tgacgatcgc atatcgtcag tgc                            33

<210> SEQ ID NO 102
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 102
atgatctcag tcagcagcta tgtcagtgca tgc                            33

<210> SEQ ID NO 103
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 103
agtgactgat cgtcatcagc tagcatcgac tgc                            33

<210> SEQ ID NO 104
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 104
atgtagtcga gcatcatctg acgcagtacg tgc                            33

<210> SEQ ID NO 105
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 105
agtgactgat cgtcatcagc tagcatcgac tgc                            33

<210> SEQ ID NO 106
```

```
<210> SEQ ID NO 106
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 106
atagatcgca tgacgatcgc atatcgtcag tgc                                33

<210> SEQ ID NO 107
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 107
atgatctcag tcagcagcta tgtcagtgca tgc                                33

<210> SEQ ID NO 108
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 108
atgtagtcga gcatcatctg acgcagtacg tgc                                33

<210> SEQ ID NO 109
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 109
atagatcgca tgacgatcgc atatcgtcag tgc                                33

<210> SEQ ID NO 110
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 110
agtgactgat cgtcatcagc tagcatcgac tgc                                33

<210> SEQ ID NO 111
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 111
atgatctcag tcagcagcta tgtcagtgca tgc                                33

<210> SEQ ID NO 112
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 112
```
agtgactgat cgtcatcagc tagcatcgac tgc                                      33

<210> SEQ ID NO 113
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 113
atagatcgca tgacgatcgc atatcgtcag tgc                                      33

<210> SEQ ID NO 114
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 114
atgatctcag tcagcagcta tgtcagtgca tgc                                      33

<210> SEQ ID NO 115
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 115
atgtagtcga gcatcatctg acgcagtacg tgc                                      33

<210> SEQ ID NO 116
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 116
atagatcgca tgacgatcgc atatcgtcag tgc                                      33

<210> SEQ ID NO 117
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 117
atgatctcag tcagcagcta tgtcagtgca tgc                                      33

<210> SEQ ID NO 118
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 118
agtgactgat cgtcatcagc tagcatcgac tgc                                      33

<210> SEQ ID NO 119
<211> LENGTH: 33
<212> TYPE: DNA

```
<213> ORGANISM: Artificial Sequence
<220> FEATURE:
<223> OTHER INFORMATION: An exemplary Flow Order B

<400> SEQUENCE: 119
atgtagtcga gcatcatctg acgcagtacg tgc                          33

<210> SEQ ID NO 120
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 120
atgatctcag tcagcagcta tgtcagtgca tgc                          33

<210> SEQ ID NO 121
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 121
atagatcgca tgacgatcgc atatcgtcag tgc                          33

<210> SEQ ID NO 122
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 122
atgtagtcga gcatcatctg acgcagtacg tgc                          33

<210> SEQ ID NO 123
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 123
agtgactgat cgtcatcagc tagcatcgac tgc                          33

<210> SEQ ID NO 124
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 124
atagatcgca tgacgatcgc atatcgtcag tgc                          33

<210> SEQ ID NO 125
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 125
atgtagtcga gcatcatctg acgcagtacg tgc                          33
```

<210> SEQ ID NO 126
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 126
atgatctcag tcagcagcta tgtcagtgca tgc                                33

<210> SEQ ID NO 127
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 127
agtgactgat cgtcatcagc tagcatcgac tgc                                33

<210> SEQ ID NO 128
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 128
atgatctcag tcagcagcta tgtcagtgca tgc                                33

<210> SEQ ID NO 129
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 129
agtgactgat cgtcatcagc tagcatcgac tgc                                33

<210> SEQ ID NO 130
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 130
atagatcgca tgacgatcgc atatcgtcag tgc                                33

<210> SEQ ID NO 131
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 131
atgtagtcga gcatcatctg acgcagtacg tgc                                33

<210> SEQ ID NO 132
<211> LENGTH: 33
<212> TYPE: DNA
<213> ORGANISM: Artificial Sequence
<220> FEATURE:

<223> OTHER INFORMATION: An exemplary Flow Order B

<400> SEQUENCE: 132
atgatctcag tcagcagcta tgtcagtgca tgc                                33

<210> SEQ ID NO 133
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 133
atgtagtcga gcatcatctg acgcagtacg tgc                                33

<210> SEQ ID NO 134
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 134
agtgactgat cgtcatcagc tagcatcgac tgc                                33

<210> SEQ ID NO 135
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 135
atagatcgca tgacgatcgc atatcgtcag tgc                                33

<210> SEQ ID NO 136
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 136
agtgactgat cgtcatcagc tagcatcgac tgc                                33

<210> SEQ ID NO 137
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 137
atgtagtcga gcatcatctg acgcagtacg tgc                                33

<210> SEQ ID NO 138
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 138
atagatcgca tgacgatcgc atatcgtcag tgc                                33

```
<210> SEQ ID NO 139
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 139
atgatctcag tcagcagcta tgtcagtgca tgc                                33

<210> SEQ ID NO 140
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 140
agtgactgat cgtcatcagc tagcatcgac tgc                                33

<210> SEQ ID NO 141
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 141
atgtagtcga gcatcatctg acgcagtacg tgc                                33

<210> SEQ ID NO 142
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 142
atgatctcag tcagcagcta tgtcagtgca tgc                                33

<210> SEQ ID NO 143
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 143
atagatcgca tgacgatcgc atatcgtcag tgc                                33

<210> SEQ ID NO 144
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 144
agtgactgat cgtcatcagc tagcatcgac tgc                                33

<210> SEQ ID NO 145
<211> LENGTH: 33
<212> TYPE: DNA
<213> ORGANISM: Artificial Sequence
<220> FEATURE:
<223> OTHER INFORMATION: An exemplary Flow Order B
```

```
<400> SEQUENCE: 145
atgatctcag tcagcagcta tgtcagtgca tgc                              33

<210> SEQ ID NO 146
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 146
atagatcgca tgacgatcgc atatcgtcag tgc                              33

<210> SEQ ID NO 147
<211> LENGTH: 33
<212> TYPE: DNA
<213> ORGANISM: Artificial Sequence
<220> FEATURE:
<223> OTHER INFORMATION: An exemplary Flow Order B

<400> SEQUENCE: 147
atgtagtcga gcatcatctg acgcagtacg tgc                              33
```

SYSTEM AND METHOD FOR GENERATION AND USE OF OPTIMAL NUCLEOTIDE FLOW ORDERS

RELATED APPLICATIONS

This application claims priority to U.S. Provisional Application No. 61/648,783, filed May 18, 2012, which is herein incorporated by reference in its entirety.

INCORPORATION-BY-REFERENCE OF SEQUENCE LISTING

The contents of the text file named "21465-553001US_ST25.txt", which was created on May 7, 2013 and is 29 KB in size, is hereby incorporated by reference in their entirety.

FIELD OF THE INVENTION

The present invention relates to the field of molecular biology. More specifically, the invention relates to a system and method for generating and employing embodiments of flow order optimized to minimize the introduction of phasic synchrony errors in nucleic acid sequence data generated by what are generally referred to as "Sequencing-by-Synthesis" (SBS) techniques.

BACKGROUND OF THE INVENTION

Sequencing-by-synthesis (SBS) generally refers to methods for determining the identity or sequence composition of one or more nucleotides in a nucleic acid sample, wherein the methods comprise the stepwise synthesis of a single strand of polynucleotide molecule complementary to a template nucleic acid molecule whose nucleotide sequence composition is to be determined. For example, SBS techniques typically operate by adding a single nucleic acid (also referred to as a nucleotide) species to a nascent polynucleotide molecule complementary to a nucleic acid species of a template molecule at a corresponding sequence position. The addition of the nucleic acid species to the nascent molecule is generally detected using a variety of methods known in the art that include, but are not limited to what are referred to as pyrosequencing which may include enzymatic or electronic (i.e. pH detection with ISFET or other related technology) detection strategies or fluorescent detection methods that in some embodiments may employ reversible terminators. Typically, the process is iterative until a complete (i.e. all sequence positions are represented) or desired sequence length complementary to the template is synthesized. Some examples of SBS techniques are described in U.S. Pat. Nos. 6,274,320; 7,211,390; 7,244,559; 7,264,929; and 7,335,762 each of which is hereby incorporated by reference herein in its entirety for all purposes.

In some embodiments of SBS, an oligonucleotide primer is designed to anneal to a predetermined, complementary position of the sample template molecule. The primer/template complex is presented with a nucleotide species in the presence of a nucleic acid polymerase enzyme. If the nucleotide species is complementary to the nucleic acid species corresponding to a sequence position on the sample template molecule that is directly adjacent to the 3' end of the oligonucleotide primer, then the polymerase will extend the primer with the nucleotide species. Alternatively, in some embodiments the primer/template complex is presented with a plurality of nucleotide species of interest (typically A, G, C, and T) at once, and the nucleotide specie that is complementary at the corresponding sequence position on the sample template molecule directly adjacent to the 3' end of the oligonucleotide primer is incorporated. As described above, incorporation of the nucleotide species can be detected by a variety of methods known in the art, e.g. by detecting the release of pyrophosphate (PPi) or Hydrogen ($H^+$) enzymatically or electronically (examples described in U.S. Pat. Nos. 6,210,891; 6,258,568; and 6,828,100, each of which is hereby incorporated by reference herein in its entirety for all purposes), or via detectable labels bound to the nucleotides. In typical embodiments, unincorporated nucleotides are removed, for example by washing. In the embodiments where detectable labels are used, they will typically have to be inactivated (e.g. by chemical cleavage or photobleaching) prior to the following cycle of synthesis. The next sequence position in the template/polymerase complex can then be queried with another nucleotide species, or a plurality of nucleotide species of interest, as described above. Repeated cycles of nucleotide addition, primer extension, signal acquisition, and washing result in a determination of the nucleotide sequence of the template strand.

In typical embodiments of SBS, a large number or "clonal" population of substantially identical template molecules (e.g. $10^3$, $10^4$, $10^5$, $10^6$ or $10^7$ molecules) are analyzed simultaneously in any one sequencing reaction, in order to achieve a signal which is strong enough for reliable detection. What is referred to as "homogeneous extension" of nascent molecules associated with substantially all template molecules in a population of a given reaction is required for low signal-to-noise ratios. The term "homogeneous extension", as used herein, generally refers to the relationship or phase of the extension reaction where each member of a population of substantially identical template molecules described above are homogenously performing the same step in the reaction. For example, each extension reaction associated with the population of template molecules may be described as being in phase (also sometime referred to as phasic synchrony or phasic synchronism) with each other when they are performing the same reaction step at the same sequence position for each of the associated template molecules.

However those of ordinary skill in the related art will appreciate that a small fraction of template molecules in each population loses or falls out of phasic synchronism with the rest of the template molecules in the population (that is, the reactions associated with the fraction of template molecules either get ahead of, or fall behind, the other template molecules in the sequencing reaction on the population (some examples are described in Ronaghi, M. Pyrosequencing sheds light on DNA sequencing. Genome Res. 11, 3-11 (2001), which is hereby incorporated by reference herein in its entirety for all purposes). For example, the failure of the reaction to properly incorporate of one or more nucleotide species into one or more nascent molecules for extension of the sequence by one position results in each subsequent reaction being at a sequence position that is behind and out of phase with the sequence position of the rest of the population. This effect is referred to herein as "incomplete extension" (IE). Alternatively, the improper extension of a nascent molecule by incorporation of one or more nucleotide species in a sequence position that is ahead and out of phase with the sequence position of the rest of the population is referred to herein as "carry forward" (CF). The combined effects of CF and IE are referred to herein as CAFIE.

Those of ordinary skill will appreciate that a potential for both IE and CF errors may occur at each sequence position during an extension reaction and thus may have cumulative effects evident in the resulting sequence data. For example, the effects may become especially noticeable towards the end of a "sequence read".

Further, IE and CF effects may impose an upper limit to the length of a template molecule that may be reliably sequenced (sometimes referred to as the "read length") using SBS approaches, because the quality of the sequence data decreases as the read length increases.

Some embodiments of SBS have successfully applied numerical modeling and simulation methods to sequence data from SBS sequencing strategies to bioinformaticly correct the CAFIE error in the sequence data to extend the useable read length from a sequencing run. However, such methods are compensatory for the accumulated CAFIE error that is found in sequence reads from SBS sequencing strategies, and does not provide a mechanism for reducing the accumulation of CAFIE error during the sequencing run.

Embodiments of SBS as described herein serially introduce each nucleotide species individually into the sequencing reaction environment according to a predetermined order (also referred to as "flow order", "flow pattern", or "nucleotide dispensation order"). For example, an embodiment of SBS may employ a repeating cycle of a pre-determined order of 4 nucleotide species such as a TACG order of nucleotide species flows per cycle. In some embodiments the flow order may be repeated 200 to 400 times depending on application. However, in practice a flow order does not need to be a 4 nucleotide species cyclic repeat, such as TACG described above. In fact, some SBS applications have utilized customized flow orders which are tailored to the nucleotide sequences of an amplicon whose sequence are known a priori to maximize the number of incorporated bases that are extended by a minimum number of nucleotide species flows (i.e. have a very high extension rate by design). In the described amplicon-type flow order embodiments the flow order may be interpreted as a single flow order (i.e. non-cyclic) defined by the sequence composition of the amplicon sequence.

It is therefore desirable to extend the concepts of numerical CAFIE correction and customized flow order design and implement one or more flow orders that reduce the accumulation of CAFIE type error or can correct for some CAFIE error during a sequencing run. In other words, as opposed to applying the CAFIE correction methods to the sequencing data, the algorithms and modeling can be used to predict more optimal flow orders that reduce the accumulation of CAFIE error and/or correct some CAFIE error during the sequencing run.

A number of references are cited herein, the entire disclosures of which are incorporated herein, in their entirety, by reference for all purposes. Further, none of these references, regardless of how characterized above, is admitted as prior art to the invention of the subject matter claimed herein.

SUMMARY OF THE INVENTION

Embodiments of the invention relate to the determination of the sequence of nucleic acids. More particularly, embodiments of the invention relate to recursive methods and systems for correcting phasic synchrony errors in data obtained during the sequencing of nucleic acids by SBS.

An embodiment of a method for generating a flow order that minimizes the accumulation of phasic synchrony error in sequence data is described that comprises the steps of: (a) generating a plurality of sequential orderings of nucleotides species comprising a k-base length, wherein the sequential orderings define a sequence of introduction of nucleotide species into a sequencing by synthesis reaction environment; (b) simulating acquisition of sequence data from one or more reference genomes using the sequential orderings, wherein the sequence data comprises an accumulation of phasic synchrony error; and (c) selecting one or more of the sequential orderings using a read length parameter and an extension rate parameter.

A further embodiment of a method for sequencing a nucleic acid template using a flow order that minimizes the accumulation of phasic synchrony error in sequence data is described that comprises the steps of: (a) introducing a sequential ordering of nucleotide species comprising a k-base length into a sequencing by synthesis reaction environment, wherein the sequential ordering of nucleotide species comprises a high read length characteristic and a low extension rate characteristic; (b) acquiring signals from the sequencing by synthesis reaction environment in response to incorporation of the nucleotide species in an extension reaction of one or more populations of substantially identical nucleic acid template molecules, wherein the signals comprise a measure of error from a subset of nucleic acid template molecules from one or more of the populations fall behind a phase of extension; (c) cyclically repeating the introduction of the sequential ordering of nucleotide species and acquisition of signals for a number of iterations, wherein the subset of nucleic acid molecules re-synchronize with the phase of extension that reduces the measure of error due to the high read length characteristic and a low extension rate characteristics of the sequential ordering.

Also, another of a method for sequencing a nucleic acid template using a flow order that minimizes the accumulation of phasic synchrony error in sequence data is described that comprises the steps of: (a) introducing a sequential ordering of nucleotide species into a sequencing by synthesis reaction environment; (b) acquiring a plurality of first signals from the sequencing by synthesis reaction environment in response to incorporation of the nucleotide species in an extension reaction of one or more populations of substantially identical nucleic acid template molecules; (c) selecting a second sequential ordering of nucleotide species using the first signals, wherein the second sequential ordering of nucleotide species comprises a k-base length a, a high read length characteristic, and a low extension rate characteristic; (d) introducing the second sequential ordering of nucleotide species into the sequencing by synthesis reaction environment; (e) acquiring a plurality of second signals from the sequencing by synthesis reaction environment in response to incorporation of the nucleotide species in an extension reaction of one or more populations of substantially identical nucleic acid template molecules, wherein the second signals comprise a measure of error from a subset of nucleic acid template molecules from one or more of the populations fall behind a phase of extension; (f) cyclically repeating the introduction of the second sequential ordering of nucleotide species and acquisition of signals for a number of iterations, wherein the subset of nucleic acid molecules re-synchronize with the phase of extension that reduces the measure of error due to the high read length characteristic and a low extension rate characteristics of the sequential ordering.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures, elements, or method steps and the leftmost digit of a reference numeral indicates the number of the figure in which the references element first appears (for example, element 160 appears first in FIG. 1). All of these conventions, however, are intended to be typical or illustrative, rather than limiting.

DETAILED DESCRIPTION OF THE INVENTION

Figure 1:
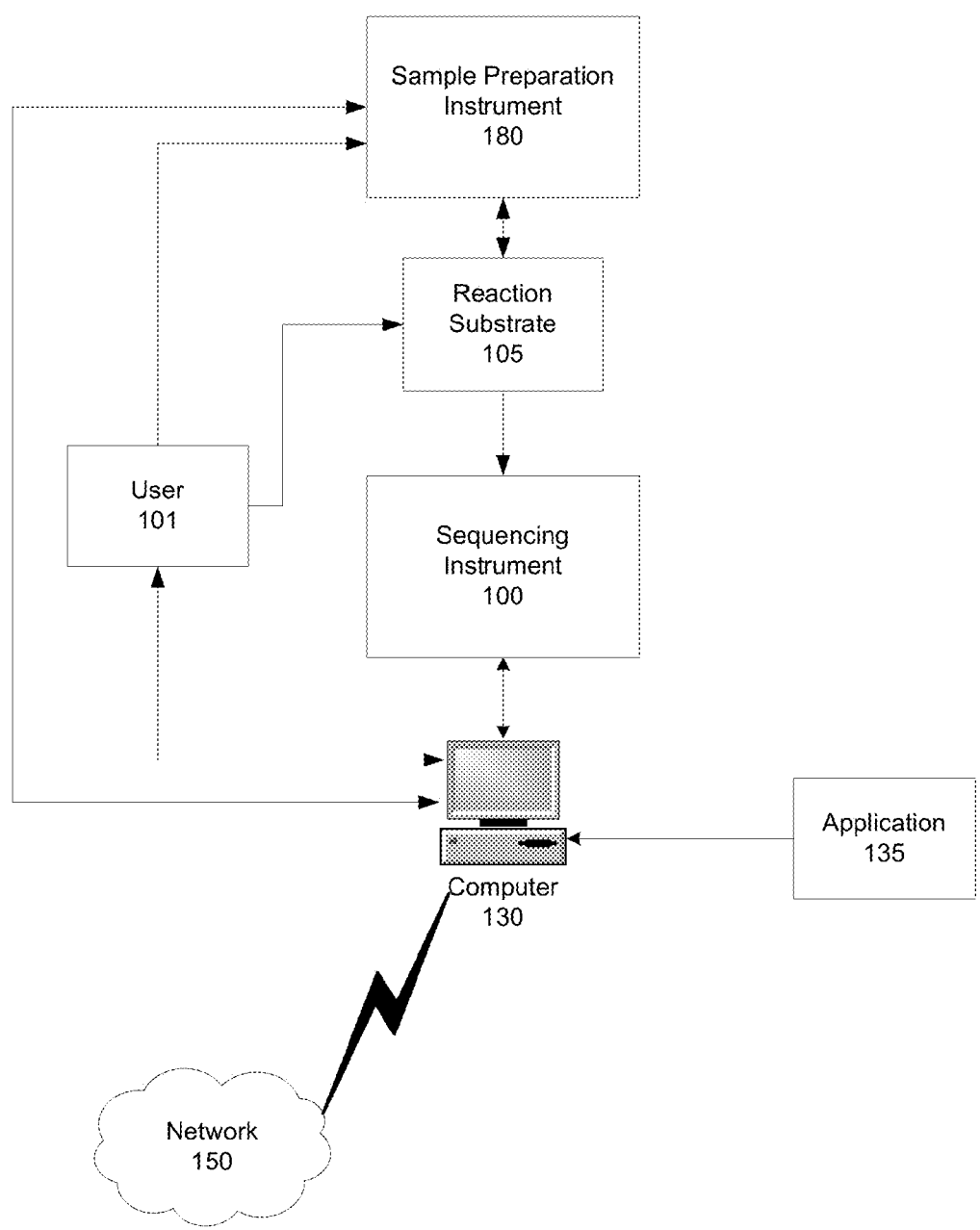
FIG. 1 is a functional block diagram of one embodiment of a sequencing instrument under computer control and a reaction substrate.

As will be described in greater detail below, embodiments of the presently described invention include systems and methods for generating and employing embodiments of flow order optimized to minimize phasic synchrony errors in nucleic acid sequence data generated by what are generally referred to as "Sequencing-by-Synthesis" (SBS) techniques. The "phasic synchrony flow order" as described herein can be any length with a sequence composition computed to reduce the accumulation of CAFIE error, at least in part by dynamically correcting for some introduced CAFIE error during the sequencing and data acquisition process. It will also be appreciated that the phasic synchrony flow order may be a single flow order for an entire sequencing run or a flow order of shorter length that is iterated cyclically.

a. General

Unless otherwise defined, all technical and scientific terms used herein have the same meaning as commonly understood by one of ordinary skill in the art to which this invention belongs. Methods and materials similar or equivalent to those described herein can be used in the practice of the present invention, and exemplified suitable methods and materials are described below. For example, methods may be described which comprise more than two steps. In such methods, not all steps may be required to achieve a defined goal and the invention envisions the use of isolated steps to achieve these discrete goals. The disclosures of all publications, patent applications, patents, and other references are incorporated in toto herein by reference. In addition, the materials, methods, and examples are illustrative only and not intended to be limiting.

The term "flowgram" generally refers to a graphical representation of sequence data generated by SBS methods, particularly pyrophosphate based sequencing methods (also referred to as "pyrosequencing") and may be referred to more specifically as a "pyrogram".

The term "read" or "sequence read" as used herein generally refers to the entire sequence data obtained from a single nucleic acid template molecule or a population of a plurality of substantially identical copies of the template nucleic acid molecule.

The terms "run" or "sequencing run" as used herein generally refer to a series of sequencing reactions performed in a sequencing operation of one or more template nucleic acid molecules.

The term "flow" as used herein generally refers to a single introduction of a nucleotide species or reagent into a reaction environment that is typically part of an iterative sequencing by synthesis process comprising a template nucleic acid molecule. For example, a flow may include a solution comprising a nucleotide species and/or one or more other reagents, such as buffers, wash solutions, or enzymes that may be employed in a sequencing process or to reduce carryover or noise effects from previous flows of nucleotide species.

The term "flow order", "flow pattern", or "nucleotide dispensation order" as used herein generally refers to a pre-determined series of flows of a nucleotide species into a reaction environment. In some embodiments a flow cycle may include a sequential addition of 4 nucleotide species in the order of T, A, C, G nucleotide species, or other order where one or more of the nucleotide species may be repeated.

The term "flow cycle" as used herein generally refers to an iteration of a flow order where in some embodiments the flow cycle is a repeating cycle having the same flow order from cycle to cycle, although in some embodiments the flow order may vary from cycle to cycle.

The term "read length" as used herein generally refers to an upper limit of the length of a template molecule that may be reliably sequenced. There are numerous factors that contribute to the read length of a system and/or process including, but not limited to the degree of GC content in a template nucleic acid molecule.

The term "signal droop" as used herein generally refers to a decline in detected signal intensity as read length increases.

The term "test fragment" or "TF" as used herein generally refers to a nucleic acid element of known sequence composition that may be employed for quality control, calibration, or other related purposes.

The term "primer" as used herein generally refers to an oligonucleotide that acts as a point of initiation of DNA synthesis under conditions in which synthesis of a primer extension product complementary to a nucleic acid strand is induced in an appropriate buffer at a suitable temperature. A primer is preferably a single stranded oligodeoxyribonucleotide.

A "nascent molecule" generally refers to a DNA strand which is being extended by the template-dependent DNA polymerase by incorporation of nucleotide species which are complementary to the corresponding nucleotide species in the template molecule.

The terms "template nucleic acid", "template molecule", "target nucleic acid", or "target molecule" generally refer to a nucleic acid molecule that is the subject of a sequencing reaction from which sequence data or information is generated.

The term "nucleotide species" as used herein generally refers to the identity of a nucleic acid monomer including purines (Adenine, Guanine) and pyrimidines (Cytosine, Uracil, Thymine) typically incorporated into a nascent nucleic acid molecule. "Natural" nucleotide species include, e.g., adenine, guanine, cytosine, uracil, and thymine. Modified versions of the above natural nucleotide species include, without limitation, alpha-thio-triphosphate derivatives (such as dATP alpha S), hypoxanthine, xanthine, 7-methylguanine, 5,6-dihydrouracil, and 5-methylcytosine.

The term "monomer repeat" or "homopolymers" as used herein generally refers to two or more sequence positions comprising the same nucleotide species (i.e. a repeated nucleotide species).

The term "homogeneous extension" as used herein generally refers to the relationship or phase of an extension reaction where each member of a population of substantially identical template molecules is homogenously performing the same extension step in the reaction.

The term "completion efficiency" as used herein generally refers to the percentage of nascent molecules that are properly extended during a given flow.

The term "incomplete extension rate" as used herein generally refers to the ratio of the number of nascent molecules that fail to be properly extended over the number of all nascent molecules.

The term "genomic library" or "shotgun library" as used herein generally refers to a collection of molecules derived from and/or representing an entire genome (i.e. all regions of a genome) of an organism or individual.

The term "amplicon" as used herein generally refers to selected amplification products, such as those produced from Polymerase Chain Reaction or Ligase Chain Reaction techniques.

The term "variant" or "allele" as used herein generally refers to one of a plurality of species each encoding a similar sequence composition, but with a degree of distinction from each other. The distinction may include any type of variation known to those of ordinary skill in the related art, that include, but are not limited to, polymorphisms such as single nucleotide polymorphisms (SNPs), insertions or deletions (the combination of insertion/deletion events are also referred to as "indels"), differences in the number of repeated sequences (also referred to as tandem repeats), and structural variations.

The term "allele frequency" or "allelic frequency" as used herein generally refers to the proportion of all variants in a population that is comprised of a particular variant.

The term "key sequence" or "key element" as used herein generally refers to a nucleic acid sequence element (typically of about 4 sequence positions, i.e., TGAC or other combination of nucleotide species) associated with a template nucleic acid molecule in a known location (i.e., typically included in a ligated adaptor element) comprising known sequence composition that is employed as a quality control reference for sequence data generated from template molecules. The sequence data passes the quality control if it includes the known sequence composition associated with a Key element in the correct location.

The term "keypass" or "keypass well" as used herein generally refers to the sequencing of a full length nucleic acid test sequence of known sequence composition (i.e., a "test fragment" or "TF" as referred to above) in a reaction well, where the accuracy of the sequence derived from TF sequence and/or Key sequence associated with the TF or in an adaptor associated with a target nucleic acid is compared to the known sequence composition of the TF and/or Key and used to measure of the accuracy of the sequencing and for quality control. In typical embodiments, a proportion of the total number of wells in a sequencing run will be keypass wells which may, in some embodiments, be regionally distributed.

The term "blunt end" as used herein is interpreted consistently with the understanding of one of ordinary skill in the related art, and generally refers to a linear double stranded nucleic acid molecule having an end that terminates with a pair of complementary nucleotide base species, where a pair of blunt ends are typically compatible for ligation to each other.

The term "sticky end" or "overhang" as used herein is interpreted consistently with the understanding of one of ordinary skill in the related art, and generally refers to a linear double stranded nucleic acid molecule having one or more unpaired nucleotide species at the end of one strand of the molecule, where the unpaired nucleotide species may exist on either strand and include a single base position or a plurality of base positions (also sometimes referred to as "cohesive end").

The term "SPRI" as used herein is interpreted consistently with the understanding of one of ordinary skill in the related art, and generally refers to the patented technology of "Solid Phase Reversible Immobilization" wherein target nucleic acids are selectively precipitated under specific buffer conditions in the presence of beads, where said beads are often carboxylated and paramagnetic. The precipitated target nucleic acids immobilize to said beads and remain bound until removed by an elution buffer according to the operator's needs (DeAngelis, Margaret M. et al: Solid-Phase Reversible Immobilization for the Isolation of PCR Products. *Nucleic Acids Res* (1995), Vol. 23:22; 4742-4743, which is hereby incorporated by reference herein in its entirety for all purposes).

The term "carboxylated" as used herein is interpreted consistently with the understanding of one of ordinary skill in the related art, and generally refers to the modification of a material, such as a microparticle, by the addition of at least one carboxl group. A carboxyl group is either COOH or COO—.

The term "paramagnetic" as used herein is interpreted consistently with the understanding of one of ordinary skill in the related art, and generally refers to the characteristic of a material wherein said material's magnetism occurs only in the presence of an external, applied magnetic field and does not retain any of the magnetization once the external, applied magnetic field is removed.

The term "bead" or "bead substrate" as used herein generally refers to any type of solid phase particle of any convenient size, of irregular or regular shape and which is fabricated from any number of known materials such as cellulose, cellulose derivatives, acrylic resins, glass, silica gels, polystyrene, gelatin, polyvinyl pyrrolidone, co-polymers of vinyl and acrylamide, polystyrene cross-linked with divinylbenzene or the like (as described, e.g., in Merrifield, Biochemistry 1964, 3, 1385-1390), polyacrylamides, latex gels, polystyrene, dextran, rubber, silicon, plastics, nitrocellulose, natural sponges, silica gels, control pore glass, metals, cross-linked dextrans (e.g., Sephadex™) agarose gel (Sepharose™), and other solid phase bead supports known to those of skill in the art although it will be appreciated that solid phase substrates may include a degree of porosity enabling penetration of fluids and/or biological molecule into the pores.

The term "reaction environment" as used herein generally refers to a volume of space in which a reaction can take place typically where reactants are at least temporarily contained or confined allowing for detection of at least one reaction product. Examples of a reaction environment include but are not limited to cuvettes, tubes, bottles, as well as one or more depressions, wells, or chambers on a planar or non-planar substrate.

The term "virtual terminator" as used herein generally refers to terminators substantially slow reaction kinetics where additional steps may be employed to stop the reaction such as the removal of reactants.

Some exemplary embodiments of systems and methods associated with sample preparation and processing, generation of sequence data, and analysis of sequence data are generally described below, some or all of which are amenable for use with embodiments of the presently described invention. In particular, the exemplary embodiments of systems and methods for preparation of template nucleic acid molecules, amplification of template molecules, generating target specific amplicons and/or genomic libraries, sequencing methods and instrumentation, and computer systems are described.

In typical embodiments, the nucleic acid molecules derived from an experimental or diagnostic sample should be prepared and processed from its raw form into template molecules amenable for high throughput sequencing. The processing methods may vary from application to application, resulting in template molecules comprising various characteristics. For example, in some embodiments of high throughput sequencing, it is preferable to generate template molecules with a sequence or read length that is at least comparable to the length that a particular sequencing method can accurately produce sequence data for. In the present example, the length may include a range of about 25-30 bases, about 50-100 bases, about 200-300 bases, about 350-500 bases, about 500-1000 bases, greater than 1000 bases, or any other length amenable for a particular sequencing application. In some embodiments, nucleic acids from a sample, such as a genomic sample, are fragmented using a number of methods known to those of ordinary skill in the art. In preferred embodiments, methods that randomly fragment (i.e. do not select for specific sequences or regions) nucleic acids and may include what is referred to as nebulization or sonication methods. It will, however, be appreciated that other methods of fragmentation, such as digestion using restriction endonucleases, may be employed for fragmentation purposes. Also in the present example, some processing methods may employ size selection methods known in the art to selectively isolate nucleic acid fragments of the desired length.

Also, it is preferable in some embodiments to associate additional functional elements with each template nucleic acid molecule. The elements may be employed for a variety of functions including, but not limited to, primer sequences for amplification and/or sequencing methods, quality control elements (i.e. such as Key elements or other type of quality control element), unique identifiers (also referred to as a multiplex identifier or "MID") that encode various associations such as with a sample of origin or patient, or other functional element.

For example, some embodiments of the described invention comprise associating one or more embodiments of an MID element having a known and identifiable sequence composition with a sample, and coupling the embodiments of MID element with template nucleic acid molecules from the associated samples. The MID coupled template nucleic acid molecules from a number of different samples are pooled into a single "Multiplexed" sample or composition that can then be efficiently processed to produce sequence data for each MID coupled template nucleic acid molecule. The sequence data for each template nucleic acid is de-convoluted to identify the sequence composition of coupled MID elements and association with sample of origin identified. In the present example, a multiplexed composition may include representatives from about 384 samples, about 96 samples, about 50 samples, about 20 samples, about 16 samples, about 12 samples, about 10 samples, or other number of samples. Each sample may be associated with a different experimental condition, treatment, species, or individual in a research context. Similarly, each sample may be associated with a different tissue, cell, individual, condition, drug or other treatment in a diagnostic context. Those of ordinary skill in the related art will appreciate that the numbers of samples listed above are provided for exemplary purposes and thus should not be considered limiting.

In preferred embodiments, the sequence composition of each MID element is easily identifiable and resistant to introduced error from sequencing processes. Some embodiments of MID element comprise a unique sequence composition of nucleic acid species that has minimal sequence similarity to a naturally occurring sequence. Alternatively, embodiments of a MID element may include some degree of sequence similarity to naturally occurring sequence.

Also, in preferred embodiments, the position of each MID element is known relative to some feature of the template nucleic acid molecule and/or adaptor elements coupled to the template molecule. Having a known position of each MID is useful for finding the MID element in sequence data and interpretation of the MID sequence composition for possible errors and subsequent association with the sample of origin.

For example, some features useful as anchors for positional relationship to MID elements may include, but are not limited to, the length of the template molecule (i.e. the MID element is known to be so many sequence positions from the 5' or 3' end), recognizable sequence markers such as a Key element and/or one or more primer elements positioned adjacent to a MID element. In the present example, the Key and primer elements generally comprise a known sequence composition that typically does not vary from sample to sample in the multiplex composition and may be employed as positional references for searching for the MID element. An analysis algorithm implemented by application 135 may be executed on computer 130 to analyze generated sequence data for each MID coupled template to identify the more easily recognizable Key and/or primer elements, and extrapolate from those positions to identify a sequence region presumed to include the sequence of the MID element. Application 135 may then process the sequence composition of the presumed region and possibly some distance away in the flanking regions to positively identify the MID element and its sequence composition.

Some or all of the described functional elements may be combined into adaptor elements that are coupled to nucleotide sequences in certain processing steps. For example, some embodiments may associate priming sequence elements or regions comprising complementary sequence composition to primer sequences employed for amplification and/or sequencing. Further, the same elements may be employed for what may be referred to as "strand selection" and immobilization of nucleic acid molecules to a solid phase substrate. In some embodiments, two sets of priming sequence regions (hereafter referred to as priming sequence A, and priming sequence B) may be employed for strand selection, where only single strands having one copy of priming sequence A and one copy of priming sequence B is selected and included as the prepared sample. In alternative embodiments, design characteristics of the adaptor elements eliminate the need for strand selection. The same priming sequence regions may be employed in methods for amplification and immobilization where, for instance, priming sequence B may be immobilized upon a solid substrate and amplified products are extended therefrom.

Additional examples of sample processing for fragmentation, strand selection, and addition of functional elements and adaptors are described in U.S. patent application Ser. No. 10/767,894, titled "Method for preparing single-stranded DNA libraries", filed Jan. 28, 2004; U.S. patent application Ser. No. 12/156,242, titled "System and Method for Identification of Individual Samples from a Multiplex Mixture", filed May 29, 2008; and U.S. patent application Ser. No. 12/380,139, titled "System and Method for Improved Processing of Nucleic Acids for Production of Sequencable Libraries", filed Feb. 23, 2009, each of which is hereby incorporated by reference herein in its entirety for all purposes.

Various examples of systems and methods for performing amplification of template nucleic acid molecules to generate populations of substantially identical copies are described. It will be apparent to those of ordinary skill that it is desirable in some embodiments of SBS to generate many copies of each nucleic acid element to generate a stronger signal when one or more nucleotide species is incorporated into each nascent molecule associated with a copy of the template molecule. There are many techniques known in the art for generating copies of nucleic acid molecules such as, for instance, amplification using what are referred to as bacterial vectors, "Rolling Circle" amplification (described in U.S. Pat. Nos. 6,274,320 and 7,211,390, incorporated by reference above) and Polymerase Chain Reaction (PCR) methods, each of the techniques are applicable for use with the presently described invention. One PCR technique that is particularly amenable to high throughput applications include what are referred to as emulsion PCR methods (also referred to as emPCR methods).

Typical embodiments of emulsion PCR methods include creating a stable emulsion of two immiscible substances creating aqueous droplets within which reactions may occur. In particular, the aqueous droplets of an emulsion amenable for use in PCR methods may include a first fluid, such as a water based fluid suspended or dispersed as droplets (also referred to as a discontinuous phase) within another fluid, such as a hydrophobic fluid (also referred to as a continuous phase) that typically includes some type of oil. Examples of oil that may be employed include, but are not limited to, mineral oils, silicone based oils, or fluorinated oils.

Further, some emulsion embodiments may employ surfactants that act to stabilize the emulsion, which may be particularly useful for specific processing methods such as PCR. Some embodiments of surfactant may include one or more of a silicone or fluorinated surfactant. For example, one or more non-ionic surfactants may be employed that include, but are not limited to, sorbitan monooleate (also referred to as Span 80), polyoxyethylenesorbitsan monooleate (also referred to as Tween 80), or in some preferred embodiments, dimethicone copolyol (also referred to as Abil EM90), polysiloxane, polyalkyl polyether copolymer, polyglycerol esters, poloxamers, and PVP/hexadecane copolymers (also referred to as Unimer U-151), or in more preferred embodiments, a high molecular weight silicone polyether in cyclopentasiloxane (also referred to as DC 5225C available from Dow Corning).

The droplets of an emulsion may also be referred to as compartments, microcapsules, microreactors, microenvironments, or other name commonly used in the related art. The aqueous droplets may range in size depending on the composition of the emulsion components or composition, contents contained therein, and formation technique employed. The described emulsions create the microenvironments within which chemical reactions, such as PCR, may be performed. For example, template nucleic acids and all reagents necessary to perform a desired PCR reaction may be encapsulated and chemically isolated in the droplets of an emulsion. Additional surfactants or other stabilizing agent may be employed in some embodiments to promote additional stability of the droplets as described above. Thermocycling operations typical of PCR methods may be executed using the droplets to amplify an encapsulated nucleic acid template resulting in the generation of a population comprising many substantially identical copies of the template nucleic acid. In some embodiments, the population within the droplet may be referred to as a "clonally isolated", "compartmentalized", "sequestered", "encapsulated", or "localized" population. Also in the present example, some or all of the described droplets may further encapsulate a solid substrate such as a bead for attachment of template and amplified copies of the template, amplified copies complementary to the template, or combination thereof. Further, the solid substrate may be enabled for attachment of other type of nucleic acids, reagents, labels, or other molecules of interest.

After emulsion breaking and bead recovery, it may also be desirable in typical embodiments to "enrich" for beads having a successfully amplified population of substantially identical copies of a template nucleic acid molecule immobilized thereon. For example, a process for enriching for "DNA positive" beads may include hybridizing a primer species to a region on the free ends of the immobilized amplified copies, typically found in an adaptor sequence, extending the primer using a polymerase mediated extension reaction, and binding the primer to an enrichment substrate such as a magnetic or sepharose bead. A selective condition may be applied to the solution comprising the beads, such as a magnetic field or centrifugation, where the enrichment bead is responsive to the selective condition and is separated from the "DNA negative" beads (i.e. NO: or few immobilized copies).

Embodiments of an emulsion useful with the presently described invention may include a very high density of droplets or microcapsules enabling the described chemical reactions to be performed in a massively parallel way. Additional examples of emulsions employed for amplification and their uses for sequencing applications are described in U.S. Pat. Nos. 7,638,276; 7,622,280; 7,842,457; 7,927, 797; and 8,012,690 and U.S. patent application Ser. No. 13/033,240, each of which is hereby incorporated by reference herein in its entirety for all purposes.

Also embodiments sometimes referred to as Ultra-Deep Sequencing, generate target specific amplicons for sequencing may be employed with the presently described invention that include using sets of specific nucleic acid primers to amplify a selected target region or regions from a sample comprising the target nucleic acid. Further, the sample may include a population of nucleic acid molecules that are known or suspected to contain sequence variants comprising sequence composition associated with a research or diagnostic utility where the primers may be employed to amplify and provide insight into the distribution of sequence variants in the sample. For example, a method for identifying a sequence variant by specific amplification and sequencing of multiple alleles in a nucleic acid sample may be performed. The nucleic acid is first subjected to amplification by a pair of PCR primers designed to amplify a region surrounding the region of interest or segment common to the nucleic acid population. Each of the products of the PCR reaction (first amplicons) is subsequently further amplified individually in separate reaction vessels such as an emulsion based vessel described above. The resulting amplicons (referred to herein as second amplicons), each derived from one member of the first population of amplicons, are sequenced and the collection of sequences are used to determine an allelic frequency of one or more variants present. Importantly, the method does not require previous knowledge of the variants present and can typically identify variants present at <1% frequency in the population of nucleic acid molecules.

Some advantages of the described target specific amplification and sequencing methods include a higher level of sensitivity than previously achieved and are particularly useful for strategies comprising mixed populations of template nucleic acid molecules. Further, embodiments that employ high throughput sequencing instrumentation, such as for instance embodiments that employ what is referred to as a PicoTiterPlate array (also sometimes referred to as a PTP plate or array) of wells provided by 454 Life Sciences Corporation, the described methods can be employed to generate sequence composition for over 100,000, over 300,000, over 500,000, or over 1,000,000 nucleic acid regions per run or experiment and may depend, at least in part, on user preferences such as lane configurations enabled by the use of gaskets, etc. Also, the described methods provide a sensitivity of detection of low abundance alleles which may represent 1% or less of the allelic variants present in a sample. Another advantage of the methods includes generating data comprising the sequence of the analyzed region. Importantly, it is not necessary to have prior knowledge of the sequence of the locus being analyzed.

Additional examples of target specific amplicons for sequencing are described in U.S. patent application Ser. No. 11/104,781, titled "Methods for determining sequence variants using ultra-deep sequencing", filed Apr. 12, 2005; PCT Patent Application Serial No. US 2008/003424, titled "System and Method for Detection of HIV Drug Resistant Variants", filed Mar. 14, 2008; and U.S. Pat. No. 7,888,034, titled "System and Method for Detection of HIV Tropism Variants", filed Jun. 17, 2009; and U.S. patent application Ser. No. 12/592,243, titled "SYSTEM AND METHOD FOR DETECTION OF HIV INTEGRASE VARIANTS", filed Nov. 19, 2009, each of which is hereby incorporated by reference herein in its entirety for all purposes.

Further, embodiments of sequencing may include Sanger type techniques, techniques generally referred to as Sequencing by Hybridization (SBH), Sequencing by Ligation (SBL), or Sequencing by Incorporation (SBI) techniques. The sequencing techniques may also include what are referred to as polony sequencing techniques; nanopore, waveguide and other single molecule detection techniques; or reversible terminator techniques. As described above, a preferred technique may include Sequencing by Synthesis methods. For example, some SBS embodiments sequence populations of substantially identical copies of a nucleic acid template and typically employ one or more oligonucleotide primers designed to anneal to a predetermined, complementary position of the sample template molecule or one or more adaptors attached to the template molecule. The primer/template complex is presented with a nucleotide species in the presence of a nucleic acid polymerase enzyme. If the nucleotide species is complementary to the nucleic acid species corresponding to a sequence position on the sample template molecule that is directly adjacent to the 3' end of the oligonucleotide primer, then the polymerase will extend the primer with the nucleotide species. Alternatively, in some embodiments the primer/template complex is presented with a plurality of nucleotide species of interest (typically A, G, C, and T) at once, and the nucleotide species that is complementary at the corresponding sequence position on the sample template molecule directly adjacent to the 3' end of the oligonucleotide primer is incorporated. In either of the described embodiments, the nucleotide species may be chemically blocked (such as at the 3'-O position) to prevent further extension, and need to be deblocked prior to the next round of synthesis. It will also be appreciated that the process of adding a nucleotide species to the end of a nascent molecule is substantially the same as that described above for addition to the end of a primer.

As described above, incorporation of the nucleotide species can be detected by a variety of methods known in the art, e.g. by detecting the release of pyrophosphate (PPi) using an enzymatic reaction process to produce light or via detection the release of $H^+$ and measurement of pH change (examples described in U.S. Pat. Nos. 6,210,891; 6,258,568; and 6,828,100, each of which is hereby incorporated by reference herein in its entirety for all purposes), or via detectable labels bound to the nucleotides. Some examples of detectable labels include, but are not limited to, mass tags and fluorescent or chemiluminescent labels. In typical embodiments, unincorporated nucleotides are removed, for example by washing. Further, in some embodiments, the unincorporated nucleotides may be subjected to enzymatic degradation such as, for instance, degradation using the apyrase or pyrophosphatase enzymes as described in U.S. patent application Ser. No. 12/215,455, titled "System and Method for Adaptive Reagent Control in Nucleic Acid Sequencing", filed Jun. 27, 2008; and Ser. No. 12/322,284, titled "System and Method for Improved Signal Detection in Nucleic Acid Sequencing", filed Jan. 29, 2009; each of which is hereby incorporated by reference herein in its entirety for all purposes.

In the embodiments where detectable labels are used, they will typically have to be inactivated (e.g. by chemical cleavage or photobleaching) prior to the following cycle of synthesis. The next sequence position in the template/polymerase complex can then be queried with another nucleotide species, or a plurality of nucleotide species of interest, as described above. Repeated cycles of nucleotide addition, extension, signal acquisition, and washing result in a determination of the nucleotide sequence of the template strand. Continuing with the present example, a large number or population of substantially identical template molecules (e.g. $10^3$, $10^4$, $10^5$, $10^6$ or $10^7$ molecules) are typically analyzed simultaneously in any one sequencing reaction, in order to achieve a signal which is strong enough for reliable detection.

In addition, it may be advantageous in some embodiments to improve the read length capabilities and qualities of a sequencing process by employing what may be referred to as a "paired-end" sequencing strategy. For example, some embodiments of sequencing method have limitations on the total length of molecule from which a high quality and reliable read may be generated. In other words, the total number of sequence positions for a reliable read length may not exceed 25, 50, 100, or 500 bases depending on the sequencing embodiment employed. A paired-end sequencing strategy extends reliable read length by separately sequencing each end of a molecule (sometimes referred to as a "tag" end) that comprise a fragment of an original template nucleic acid molecule at each end joined in the center by a linker sequence. The original positional relationship of the template fragments is known and thus the data from the sequence reads may be re-combined into a single read having a longer high quality read length. Further examples of paired-end sequencing embodiments are described in U.S. Pat. No. 7,601,499, titled "Paired end sequencing"; and in U.S. patent application Ser. No. 12/322,119, titled "Paired end sequencing", filed Jan. 28, 2009, each of which is hereby incorporated by reference herein in its entirety for all purposes.

Some examples of SBS apparatus may implement some or all of the methods described above and may include one or more of a detection device such as a charge coupled device (i.e., CCD camera) or confocal type architecture for optical detection, Ion-Sensitive Field Effect Transistor (also referred to as "ISFET") or Chemical-Sensitive Field Effect Transistor (also referred to as "ChemFET") for architectures for ion or chemical detection, a microfluidics chamber or flow cell, a reaction substrate, and/or a pump and flow valves. Taking the example of pyrophosphate-based sequencing, some embodiments of an apparatus may employ a chemiluminescent detection strategy that produces an inherently low level of background noise.

In some embodiments, the reaction substrate for sequencing may include a planar substrate, such as a slide type substrate, a semiconductor chip comprising well type structures with ISFET detection elements contained therein, or waveguide type reaction substrate that in some embodiments may comprise well type structures. Further, the reaction substrate may include what is referred to as a PTP array available from 454 Life Sciences Corporation, as described above, formed from a fiber optic faceplate that is acid-etched to yield hundreds of thousands or more of very small wells each enabled to hold a population of substantially identical template molecules (i.e., some preferred embodiments comprise about 3.3 million wells on a 70×75 mm PTP array at a 35 µm well to well pitch). In some embodiments, each population of substantially identical template molecule may be disposed upon a solid substrate, such as a bead, each of which may be disposed in one of said wells. For example, an apparatus may include a reagent delivery element for providing fluid reagents to the PTP plate holders, as well as a CCD type detection device enabled to collect photons of light emitted from each well on the PTP plate. An example of reaction substrates comprising characteristics for improved signal recognition is described in U.S. Pat. No. 7,682,816, titled "THIN-FILM COATED MICROWELL ARRAYS AND METHODS OF MAKING SAME", filed Aug. 30, 2005, which is hereby incorporated by reference herein in its entirety for all purposes. Further examples of apparatus and methods for performing SBS type sequencing and pyrophosphate sequencing are described in U.S. Pat. Nos. 7,323,305 and 7,575,865, both of which are incorporated by reference above.

In addition, systems and methods may be employed that automate one or more sample preparation processes, such as the emPCR process described above. For example, automated systems may be employed to provide an efficient solution for generating an emulsion for emPCR processing, performing PCR Thermocycling operations, and enriching for successfully prepared populations of nucleic acid molecules for sequencing. Examples of automated sample preparation systems are described in U.S. Pat. No. 7,927,797; and U.S. patent application Ser. No. 13/045,210, each of which is hereby incorporated by reference herein in its entirety for all purposes.

Also, the systems and methods of the presently described embodiments of the invention may include implementation of some design, analysis, or other operation using a computer readable medium stored for execution on a computer system. For example, several embodiments are described in detail below to process detected signals and/or analyze data generated using SBS systems and methods where the processing and analysis embodiments are implementable on computer systems.

In some embodiments a data processing application includes algorithms for correcting raw sequence data for the accumulations of CAFIE error. For example, some or all of the CAIFE error factors may be accurately approximated and applied to a theoretical flowgram model to provide a representation of real data obtained from an actual sequencing run and subsequently approximate a theoretical flowgram from an observed flowgram using an inversion of a mathematical model. Thus, an approximation of error may be applied to actual sequencing data represented in an observed flowgram to produce a theoretical flowgram representing the sequence composition of a target nucleic acid with all or substantially all of the error factors removed. Additional examples of CAFIE correction embodiments are described in U.S. Pat. Nos. 8,301,394; and 8,364,417, each of which are hereby incorporated by reference herein in its entirety for all purposes.

An exemplary embodiment of a computer system for use with the presently described invention may include any type of computer platform such as a workstation, a personal computer, a server, or any other present or future computer. It will, however, be appreciated by one of ordinary skill in the art that the aforementioned computer platforms as described herein are specifically configured to perform the specialized operations of the described invention and are not considered general purpose computers. Computers typically include known components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices.

Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provides one or more graphical representations to a user. Interfaces are typically enabled to accept user inputs using means of selection or input known to those of ordinary skill in the related art.

In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework.

Those of ordinary skill in the related art will appreciate that interfaces may include one or more GUI's, CLI's or a combination thereof.

A processor may include a commercially available processor such as a Celeron, Core, or Pentium processor made by Intel Corporation, a SPARC processor made by Sun Microsystems, an Athlon, Sempron, Phenom, or Opteron processor made by AMD corporation, or it may be one of other processors that are or will become available. Some embodiments of a processor may include what is referred to as Multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows-type operating system (such as Windows XP, Windows Vista, or Windows_7) from the Microsoft Corporation; the Mac OS X operating system from Apple Computer Corp. (such as Mac OS X v10.6 "Snow Leopard" operating systems); a Unix or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices. Examples include any commonly available random access memory (RAM), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device.

In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote. In the presently described embodiment, the functional elements of a computer communicate with each other via a system bus. Some embodiments of a computer may communicate with some functional elements using network or other types of remote communications.

As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor in a known manner into system memory, or cache memory, or both, as advantageous for execution.

Also, a computer may include one or more library files, experiment data files, and an internet client stored in system memory. For example, experiment data could include data related to one or more experiments or assays such as detected signal values, or other values associated with one or more SBS experiments or processes. Additionally, an internet client may include an application enabled to accesses a remote service on another computer using a network and may for instance comprise what are generally referred to as "Web Browsers". In the present example, some commonly employed web browsers include Microsoft Internet Explorer 8 available from Microsoft Corporation, Mozilla Firefox 3.6 from the Mozilla Corporation, Safari 4 from Apple Computer Corp., Google Chrome from the Google Corporation, or other type of web browser currently known in the art or to be developed in the future. Also, in the same or other embodiments an internet client may include, or could be an element of, specialized software applications enabled to access remote information via a network such as a data processing application for biological applications.

A network may include one or more of the many various types of networks well known to those of ordinary skill in the art. For example, a network may include a local or wide area network that may employ what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

b. Embodiments of the Presently Described Invention

As described above, the described invention relates to a system and method for generating and employing embodiments of phasic synchrony flow orders designed to minimize the accumulation of phasic synchrony errors in nucleic acid sequence data generated by what are generally referred to as SBS strategies In a typical sequencing embodiment, one or more instrument elements may be employed that automate one or more process steps. For example, embodiments of a sequencing method may be executed using instrumentation to automate and carry out some or all process steps. FIG. 1 provides an illustrative example of sequencing instrument 100 that for sequencing processes requiring capture of optical signals typically comprise an optic subsystem and a fluidic subsystem for execution of sequencing reactions and data capture that occur on reaction substrate 105. It will, however, be appreciated that for sequencing processes requiring other modes of data capture (i.e. pH, temperature, electric current, electrochemical, etc.), a subsystem for the mode of data capture may be employed which are known to those of ordinary skill in the related art. For instance, a sample of template molecules may be loaded onto reaction substrate 105 by user 101 or some automated embodiment, then sequenced in a massively parallel manner using sequencing instrument 100 to produce sequence data representing the sequence composition of each template molecule. Importantly, user 101 may include any type of user of sequencing technologies.

In some embodiments, samples may be optionally prepared for sequencing in a fully automated or partially automated fashion using sample preparation instrument 180 configured to perform some or all of the necessary sample preparation steps for sequencing using instrument 100. Those of ordinary skill in the art will appreciate that sample preparation instrument 180 is provided for the purposes of illustration and may represent one or more instruments each designed to carry out some or all of the steps associated with sample preparation required for a particular sequencing assay. Examples of sample preparation instruments may include robotic platforms such as those available from Hamilton Robotics, Fluidigm Corporation, Beckman Coulter, or Caliper Life Sciences.

Further, as illustrated in FIG. 1, sequencing instrument 100 may be operatively linked to one or more external computer components, such as computer 130 that may, for instance, execute system software or firmware, such as application 135 that may provide instructional control of one or more of the instruments, such as sequencing instrument 100 or sample preparation instrument 180, and/or data analysis functions. Computer 130 may be additionally operatively connected to other computers or servers via network 150 that may enable remote operation of instrument systems and the export of large amounts of data to systems capable of storage and processing. In the present example, sequencing instrument 100 and/or computer 130 may include some or all of the components and characteristics of the embodiments generally described herein.

As described above, some previously described embodiments include systems and methods for correcting the detected signal values of each flow to account for accumulated CAFIE error by calculating the extent of phasic synchronism loss for any known sequence, assuming given levels of CF and IE.

Table 1, illustrated below, provides an example of mathematically modeled threshold values for IE and CF that provide an accuracy of 99% or better (e.g. the read is at least 99% representative of actual sequence of template molecule) for different read lengths. The predicted values presented in Table 1 illustrate the impact of CF and IE effects on sequencing accuracy for various read lengths and the extent of IE and CF error that can be tolerated to achieve a read accuracy of approximately 99%. Table 1 shows that for an uncorrected read a CF rate of no greater than 1% is permissible (assuming IE equals zero for that population) in order for a read length of about 100 sequence positions to be 99% accurate (i.e. completion efficiency of 99% or higher). Furthermore, an IE rate of no greater than 0.25% is permissible (assuming the CF rate equals zero) in order for a read length of about 100 sequence positions to be 99% accurate.

TABLE 1

Predicted rates of error resulting in 99% accuracy at different read lengths

| | Read Length (bases) | | | | | |
| --- | --- | --- | --- | --- | --- | --- |
| | 100 | | 200 | | 400 | |
| Incomplete Extension | 0.0 | 0.0025 | 0.0 | 0.0013 | 0.0 | 0.0007 |
| Carry Forward | 0.01 | 0.0 | 0.005 | 0.0 | 0.003 | 0.00 |
| Predicted Accuracy | ~99% | ~99% | ~99% | ~99% | ~99% | ~99% |

It will be understood that the values presented in Table 1 are for the purposes of illustration only and should not be considered limiting. Those of ordinary skill will appreciate that several factors may contribute to variability of values such as the genomic or reference sequences and other parameters used to formulate predictions. For example, typical embodiments of SBS methods generally achieve CF rates that range from 1-2%, while IE rates range from 0.1-0.4% (i.e. completion efficiency ranges from 99.6-99.9%). As described above, correction and/or reduction of CF and IE is desirable because the loss of phasic synchronism has a cumulative effect over the read length and degrades the quality of a read as read length increases.

In some previously described embodiments, values representing both CF and IE are assumed to be substantially constant across the entire read of a substantially identical template molecule population, such as for instance a population of template molecules residing within a single well of a PicoTiterPlate array or other type of array of wells such as ISFET type devices. This permits numerical correction of each sequence position across the entire read using two simple parameters "completion efficiency" and "carry forward" without any a priori knowledge of the actual sequence of the template molecule. Systems and methods of previously described embodiments have been found to be very effective for determining, and correcting for, the amounts of CF and IE occurring in a population of template molecules.

For example, previous embodiments of correction have been implemented that apply a correction of the signal value detected from each flow for each population of substantially identical template molecules residing in each well to account for CF and IE.

Previously described embodiments model the lack of phasic synchronism as a nonlinear mapping:

$$M(p,\varepsilon,\lambda)=q \quad \text{Equation (1):}$$

Wherein:
M is the CAFIE mapping
p is the theoretical flowgram [as array]
$\lambda$ is the completion efficiency parameter
$\varepsilon$ is the carry forward parameter
q is the observed flowgram [as array]

A theoretical flowgram can be converted into a real-life observed flowgram by use of the mapping model formula given in Equation (1) to estimate IE and CF. A model for such a mapping formula can be generated by, for example, analyzing the errors that are introduced to an observed flowgram (q) by sequencing a polynucleotide template molecule having a known sequence.

For example a theoretical flowgram (p) provides an idealized signal strength value associated a nucleotide species introduced into the reaction environment, where each idealized value of theoretical flowgram is an integer or zero. In the present example, a value of "1" represents a 100% detected signal strength elicited by a single nucleotide incorporation, and "0" represents 0% signal (e.g., in a well comprising a population of 1 million substantially identical template molecules and 1 million nascent molecules, "1" represents the signal elicited when every nascent molecule is extended by a single nucleotide, "2" represents the signal elicited when every nascent molecule is extended by two nucleotides, etc.). Alternatively, an observed (or simulated) flowgram (q) provides an actually detected signal strength value associated with a nucleotide specie introduced into the reaction environment.

In the present example the differences in signal strength values between theoretical flowgram (p) and observed flowgram (q) for each flow iteration is indicative, at least in part, of a loss of phasic synchrony. For instance, the signal values represented in observed flowgram (q) are not integers, rather each are typically slightly higher or slightly lower than ideal value represented in theoretical flowgram (p) for the same iteration of nucleotides species flow.

A mapping model, represented as "M", may be estimated using known values for the CF and IE parameters. For example, the CF and IE parameters include a $\varepsilon$ (carry-forward) parameter and a $\lambda$ (completion efficiency) parameter. The CF and IE parameters may be employed to estimate mapping model M and convert the signal values of the theoretical flowgram (p) into the values of observed flowgram (q). In the present example, the error value represented by mapping model M accumulates with each iteration of flow, and grows exponentially.

Continuing the example from above, the phasicly synchronized sequencing reactions associated with each population of substantially identical template molecules become three different phasicly synchronized sub-populations after a flow iteration. The sub-populations include: a first sub-population of phasicly synchronized reactions where the nucleotide species in the flow is properly incorporated at the appropriate sequence position relative to the template molecules (e.g. no CAFIE effects); a second sub-population of phasicly synchronized reactions where improper incorporation from CF mechanisms has occurred and the reactions are ahead of the sequence position relative of the first population; and a third sub-population of phasicly synchronized reactions where improper incorporation from IE mechanisms has occurred and the reactions are behind the sequence position of the first population. In the present example, at the next flow iteration three sub-sub-populations will form from each of the three sub-populations described above, and so on. Those of ordinary skill in the related art will appreciate that at an n-th flow iteration, there will be $3^n$ populations of phasicly synchronized reactions contributing a signal at flow n.

Further continuing the example from above, an inversion of mapping model M, may use estimations of the correct values for CF and IE parameters (e.g. a value for both the $\varepsilon$ (carry-forward) and $\lambda$ (completion efficiency) parameters), to invert the signal values of observed flowgram (q) back to give the signal values of the theoretical flowgram (p).

Some embodiments execute the inverted mapping in two consecutive stages, (i) and (ii) outlined below:
For each nucleotide specie flow i:
(i)—Extension of Nascent Molecule Through Nucleotide Species Addition:

$$\left\{ \begin{array}{c} q_i = \lambda \sum_j m_j p_j \\ (m_j, m_{j'}) \leftarrow (m_j, m_{j'}) + \lambda(-1, 1) m_j p_j \end{array} \right\}$$

for all $j$ such that $N_j = N_i$ and $p_j > 0$ (ii)—Extension of Nascent Molecule Through Nucleotide Species Leftover from a Previous Addition:

$$\left\{ \begin{array}{c} q_i \leftarrow q_j + \varepsilon \sum_j m_j p_j \\ (m_j, m_{j'}) \leftarrow (m_j, m_{j'}) + \varepsilon(-1, 1) m_j p_j \end{array} \right\}$$

for all $j$ such that $N_j = N_{i-1}$ and $p_j > 0$

Wherein:
$p_i$ is the theoretical (clean) flowgram signal value at i-th nucleotide species flow
$q_i$ is the observed flowgram signal value at i-th nucleotide species flow
$m_i$ is the fraction of nucleotide species molecules available for incorporation at a flowgram sequence position for the i-th nucleotide species flow
$N_i$ is the i-th nucleotide specie addition (A, C, G, or T)
$\varepsilon$ is the carry-forward (CF) parameter
$\lambda$ is the completion efficiency (1E) parameter
(j, j') are pair indices such that $p_{j'}$ is the next positive value of $p_j$ on the flowgram In some embodiments, the calculations using the mapping model are executed flow-by-flow, and updates observed flowgram (q), and the fraction of the template molecules, m, recursively through stages (i) and (ii).

As will be described in greater detail below, a forward matrix model may be employed to derive an inverse matrix model. For example, performing matrix calculations using an inverse matrix model may be employed to derive estimations for the correct CF and IE parameters. For instance, various values for the CF and IE parameters may be applied in the matrix calculations and evaluated for the degree of fit to an observed flowgram. Typically, the CF and IE parameters values that provide the best fit to the observed flowgram (q) are determined to be good estimates for actual values of the CF and IE parameters.

In the same example, a forward matrix calculation using a forward matrix model may be used to generate observed flowgram (q) using the CF and IE parameters that includes a completion efficiency value λ=0.95 and a carry forward value ε=0.05. Each row associated with an iteration of flow of the forward matrix records the operations and results of recursive stages (i, ii) for each nucleotide specie flow.

Equation (1) and the recursive stages (i, ii) can be rewritten as a matrix-array operation:

$$[M(p',\varepsilon,\lambda)]*p=q \quad \text{Equation (2)}$$

wherein:
[M(p', ε, λ)] is a matrix
* is the matrix-array multiplication
p' is binary encoding list of a theoretical flowgram (e.g., the flowgram p in FIG. 1, p=[0 1 0 2 0 0 1 0 3 0 1 2]$^t$ will be encoded as p'=[0 1 0 1 0 0 1 0 1 0 1 1]$^t$).

The inverse form of Equation (2) gives the inverse mapping, converting the observed flowgram (q) 103 back to theoretical flowgram (p) 101:

$$p=[M^{-1}(p',\varepsilon,\lambda)]*q \quad \text{Equation (3)}$$

wherein:
[M$^{-1}$(p', ε, λ)] is the inverse matrix

An iterative method is used solve the inverse Equation (3), to obtain the theoretical flowgram (p) for each read. This iteration is performed with a given pair of parameters (ε, λ) for the CAFIE inversion:

$$p^{(n+1)}=[M^{-1}(p'^{(n)},\varepsilon,\lambda)]*q \quad \text{Equation (4)}$$

Wherein p'$^{(1)}$=q' is used as the seed for the calculation.

Also in the presently described example, an inverse matrix calculation using an inverse matrix model may be used to generate theoretical flowgram (p) from the observed flowgram (q) using the CF and IE parameters that include a completion efficiency value λ=0.95 and a carry forward value ε=0.05.

A value of threshold is used to represent an estimation of the signal to noise ratio of the system. For example, in one implementation a fixed value, threshold=0.2, may be employed. In such an implementation, the binary encoding list q' associated with a flowgram q encodes a value "1" when the flowgram value q is greater than 0.2, and encodes a value "0" when the flowgram value q is less than or equal to 0.2. In the present example, the threshold value 0.2 is an estimation of the signal to noise ratio as described above.

Alternatively, some implementations may employ a threshold value in can be inverted back to the clean theoretical flowgram (p) through Equation (4), for a given pair of parameters (ε, λ). In many implementations, a single iteration of flowgram inversion can generally suffice. In some implementations it may be desirable to perform, 2, 3, or more iterations of flowgram inversion where the accuracy of the flowgram representation may be improved with each iteration, particularly for longer read lengths, until convergence of the calculation on a solution with a desired quality. In some embodiments, 1 or 2 iterations of flowgram inversion may be performed in the interest of computational efficiency. Also, some embodiments implemented by computer code may enable a user selection of a number of iterations to perform and/or serially perform each iteration in response to a user selection. For example, a user may perform selections using methods known in the art such as inputting values in one or more fields or selection of buttons presented in a GUI. In the present example, a user may input a value indicating a number of iterations to perform and/or the user may select a button to execute an iteration of the invention. Further, the user may select an indication of data quality where the invention iterates until the level of data quality is achieved.

In some embodiments, estimations of values for CF and IE parameters may be determined using Equation (4). For example, the best-fitting value for the completion efficiency parameter (λ) may be determined by performing test calculations using Equation (4) inputting different values for the completion efficiency parameter while using a fixed value for the CF parameter. In the present example, values of λ=1, 0.999, 0.998, . . . , 0.990, with a fixed CF value ε=0 may be successively employed and results for each obtained. In different embodiments, the 0.001 interval between input λ values may be replaced by other intervals, such as, for instance, interval values of 0.05, 0.01, 0.005, 0.001, 0.0005, 0.0001, or the like.

Continuing with the present example, if any signal value for a flow bar in a computed theoretical flowgram (p) falls below zero after solving Equation (4) using an input value for λ, then that λ value is declared as the value of the best-fitting completion efficiency parameter. Once the best fitting value of λ is determined use of subsequently smaller λ values will result in what is referred to as "over-fitting" and produce artificially-negative flow signals. Also in the present example, a corrected signal value for some flow bar at a sequence position after a long series of flow bars representing homopolymers (e.g. a series of sequence positions comprising the same nucleotide species) may fall below zero. This zero-crossing point is the best-fit completion efficiency is denoted as λ* hereafter.

Likewise, in some embodiments the effect of CF may be addressed by a similar approach. For example, values for the CF parameter may be tested that, for instance, may include values of ε=0, 0.0025, 0.005, 0.0075, 0.01, . . . , 0.04 with the completion efficiency parameter λ fixed at the previously found value λ*. In the present example, the 0.0025 interval between input values for ε is presented for the purpose of illustration and can be replaced by other small interval values such as, for instance, interval values of 0.05, 0.01, 0.005, 0.001, 0.0005, 0.0001, 0.00001, or the like. If any signal value for a flow bar in a computed theoretical flowgram (p) falls below zero after solving Equation (4) using an input value for ε (e.g., any signal value for a flow bar other than the signal value for flow bars that fell below zero during the search along the λ path), then that ε value is declared as the value of the best-fitting CF parameter. Once the best fitting value of ε is determined, use of subsequently larger values will result in over-fitting and produce artificially negative flow signals. Also in the present example, a corrected signal value for some flow bar at a sequence position before a long series of flow bars representing homopolymers may fall below zero. This zero-crossing point is the best-fit CF is denoted as ε* hereafter.

Thus, since the amounts of CF and IE, as well as the underlying template molecule sequence p, are unknown a priori, the methods of the invention can be used in a complete de-novo analysis mode. No prior knowledge of the polymerase incorporation efficiency (i.e. λ) or the effectiveness of the nucleotide wash-out (i.e. ε) is necessary; nor are any reference nucleotide sequences required to perform the inversion.

In some embodiments, the search process for parameter estimation described above constructs a matrix [M] through stages (i, ii) at every input search interval of ε and λ, which is limiting from a computational efficiency perspective.

Such limitations may be overcome, at least in part, by employing approximations on the matrix construction operation. For example, one can avoid re-constructing the matrix at every search interval and hence greatly improve the computational speed. Two such methods are described below:

Method 1:

At small values of ε and (1-λ) (e.g., (1-λ)<=0.001 and ε<=0.0025), the matrix [M] is decomposed, and approximated into a form:

$$[M(p',\varepsilon,\lambda)] \sim [L(p',\Delta\lambda)]^{\phi} * [U(p',\Delta\varepsilon)]^{\overline{\omega}} \quad \text{Equation (5):}$$

wherein:
Δε=0.0025 and Δλ=0.001, are the intervals in the ε- and λ-axis, respectively.
φ and $\overline{\omega}$ are the matrix powers, with the properties of $\overline{\omega} \sim \varepsilon/\Delta\varepsilon$ and $\phi \sim (1-\lambda)/\Delta\lambda$.
[L(p', Δλ)] is a lower diagonal matrix, which models the effect of IE at a small deficiency Δλ.
[U(p', Δλ)] is an upper diagonal matrix, which models the effect of CF at small deficiency Δε.

Through this decomposition, Equation (5) constructs the lower diagonal matrix L and upper diagonal matrix U only once along the search path, and the degrees of incompletion and carry-forward at the search grid, (ε, λ), are modeled by the powers of the matrices, ($\overline{\omega}$, φ). The small values in the search intervals, Δε=0.0025 and Δλ=0.001, may be replaced by other small values, such as, for example, 0.05, 0.01, 0.005, 0.001, 0.0005, 0.0001, or the like.

Instead of searching on (ε, λ)-grids previously exhibited, the method here stages through a set of ($\overline{\omega}$, φ)-grids, which are preferably positive integers to facilitate the computations of matrix powers. The best-fit ($\overline{\omega}$*, φ*) are defined at the zero-crossing condition; the corresponding completion efficiency and CF parameters are $\lambda^* = (1-\phi^*\Delta\lambda)$ and $\varepsilon^* = \overline{\omega}^*\Delta\varepsilon$.

Method 2:

Following Equation (5) at small ε and (1-λ) cases, the lower and upper diagonal power matrices, $[L]^{\phi}$ and $[U]^{\overline{\omega}}$, are further approximated by $$[L]^{\phi} = ([I]+[l])^{\phi} \sim [I]+\phi[l] \quad \text{Equation (6):}$$

$$[U]^{\overline{\omega}} = ([I]+[u])^{\overline{\omega}} \sim [I]+\overline{\omega}[u] \quad \text{Equation (7):}$$

wherein:
[I] is the identity matrix.
[l] and [u] are off-diagonal matrices of [L] and [U], respectively.

This formulates a by-pass of the stage of computing matrix powers, and hence provides further speed up (e.g. decrease in) in the computing time. The search space in ($\overline{\omega}$, φ) now contains all positive real numbers. The best-fit ($\overline{\omega}$*, φ*) are defined at the zero-crossing condition; the corresponding completion efficiency and CF parameters are:

$$\lambda^* = (1-\phi^*\Delta\lambda) \text{ and } \varepsilon^* = \overline{\omega}^*\Delta\varepsilon. \quad \text{Equation (8):}$$

The embodiments presented above are based on constructing and inversing the matrices, and a two-dimensional search in the (ε, λ) plane to probe the optimal pair of CAFIE parameters. These calculations typically are performed on each population of substantially identical template molecules, which for example may include a site-by-site analysis in an array of reaction sites based system (e.g. such as a PicoTiterPlate array of wells or ISFET array of wells). In some embodiments, a matrix is constructed for each population/site to produce optimal CAFIE values (ε*, λ*).

The embodiments described above also assume that the rates associated with the constant completion efficiency λ and CF ε parameters remain constant throughout the sequencing runs. This assumption can be alleviated by applying the CAFIE search and the inversion procedures on what may be referred to as "flow windows" in flowgrams that comprise several flow cycles (wherein "several" means any integer between 1 and the total number of flow cycles). For example, each flow window is a subset of the full set of flow cycles represented in a flowgram, with a pair of CAFIE parameters and a corresponding clean theoretical flowgram (p) needing to be found. In the present example, each flow window is arranged such that it starts from the first flow in the flowgram associated with a sequencing run and ends at a certain flow shorter or equal to the full length of the flow cycles in the flowgram, where each smaller flow window is nested within a larger one. For each flow window k, the search and inversion processes occur independently to produce a set of CAFIE parameters, which are now functions of window indices k: $\varepsilon^* = \varepsilon^*(k)$ and $\lambda^* = \lambda^*(k)$. The computed theoretical flowgram (p), p(k), also nested, is the result of these variable values of the CAFIE parameters depending on the indices k. A "stitching" process: p=p(k) for flows between windows (k-1) and k, re-assembles the flow window sequences p(k) into the final flowgram (p).

In the same or alternative embodiments, the assumption of constant values for λ and ε may be eliminated by another method. For example, completion efficiency λ and CF ε parameters can assume parametric forms, such as exponentials, for each nucleotide specie addition "N" ("A", "G", "C", or "T"), and as functions of flow position "i" (1, 2, 3, . . . ):

$$\lambda_N(i) = \lambda^0_N * \exp(-\delta_N * i),$$

$$\varepsilon_N(i) = \varepsilon^0_N * \exp(-\beta_N * i). \quad \text{Equations (9-10):}$$

Wherein:
$\lambda_N(i)$ is the completion efficiency of nucleotide specie "N" at "i"-th flow
$\varepsilon_N(i)$ is the CF of nucleotide specie "N" at "i"-th flow
$\lambda^0_N$ and $\varepsilon^0_N$ are the initial values
$\delta_N$ and $\beta_N$ are the attenuation rates
Search methods are applied in the four parameter spaces, $\lambda^0_N$, $\varepsilon^0_N$, $\delta_N$ and $\beta_N$, to determine the optimal values.

In addition, those of ordinary skill in the related art will also appreciate that other sources of noise not related to the described CAFIE mechanisms may exist. Such sources of noise may include, but are not limited to electronic sources such as what may be referred to as "Dark Current", optical sources, biological sources, chemical sources, or other sources known in the art or that may be discovered in the future. Some embodiments of the presently described invention may exhibit varying levels of sensitivity to the other sources of noise that may, in many applications, be at a substantially consistent and/or predictable level. For example, predictable and consistent levels of noise attributable to known or unknown sources are generally easy to correct. One method of correction is to mathematically add or subtract a value associated with the noise (depending upon whether the noise adds excess signal or reduces detected signal) from all signal values associated with a flow.

In some embodiments where the level of noise is not predictable, at least in part, estimations of the level of noise may be derived from information embedded in the signal data. For example, for nucleotide species known or predicted to not be present at a sequence position it is expected that the actual signal value should equal to zero (i.e. "zero-mer" position). Therefore, any detected signal may be attributable to all sources of noise in the system. In the present example, since the presently described embodiment estimates noise from CAFIE mechanisms such noise may be removed from the data and the underlying noise revealed. In the present example, the estimates may be improved by looking at all "zero-mer" sequence positions in a sequence run. In this case, the value of "threshold" in the binary encoding $p'^{(n)}$ Equation (4), can be dynamically determined for each run, to represent its noise level, instead of a fixed value as described in the previous embodiment above.

Even further, some previously described embodiments included what may be referred to as "safety criteria" to prevent over correction of the sequence data represented in an observed flowgram (q). As described above, over correction can cause an exponential accumulation of error introduced as the described algorithm iterates. For example, the other sources of noise described above may determine the safety criteria that include an amount of correction to be applied to the signal data. For example, some implementations may assume a given level of noise from other non-CAFIE sources and apply a safety criteria of what may be referred to as 60% correction (e.g. 100% implies full correction) to the data. This estimate uses a "hybrid" flowgram, "0.6p+0.4q", comprising 60% of the computed clean flowgram p and 40% of the observed flowgram q. Alternatively, if the non-CAFIE noise is at a "low" level a higher percentage of correction may be applied, such as for instance 80%.

In addition, further embodiments are described that provide performance improvements over the embodiments of CAFIE correction described above (hereafter referred to as "Standard CAFIE") providing significant advantages to users. As will be described in greater detail below the improved CAFIE correction methods extend upon the Standard CAFIE correction method described above by taking theoretical flowgram (p) output from Standard CAFIE and recursively re-estimating the flowgram signals until the positive incorporation list converges upon an optimized result (hereafter referred to as "Recursive CAFIE"). Upon convergence of the recursively corrected flowgram and the positive incorporation list, the Recursive CAFIE method yields better correction over the Standard CAFIE correction method described above. The improvements comprise an improved algorithm for finding the phasic synchrony CAFIE parameters and a recursive procedure to correct the phasic synchrony errors. Also in the same or alternative embodiments a Reference CAFIE correction may be employed where a consensus flow list can be taken from an organism's known reference sequence and used to estimate the threshold value as described above where positions in the binary encoding list can be predicted to have no signal based upon the corresponding sequence position in the reference sequence and thus an observed signal may be attributed to noise and/or a sequence variant from the reference sequence. It will be appreciated that the magnitude of the observed signal is generally indicative of whether it can be attributed to a sequence variant or to noise, particularly when compared to the magnitude of signal at other positions in the binary encoding list that are predicted to have no signal.

Typical embodiments of a Recursive CAFIE correction strategy first performs phasic synchrony correction on an observed flowgram from a sequence read using the Standard CAFIE correction method, and through iterations using the Recursive CAFIE algorithm producing CAFIE-corrected flowgrams, it estimates a new binary encoding list (p') which more accurately reflects the true sequence than what was derived from the observed flowgram (q). The new binary encoding list is then used to estimate again (and thus more accurately) the completion efficiency $\lambda$ and carry-forward $\varepsilon$ parameters for the sequence read. The new estimation of ($\lambda$, $\varepsilon$) is achieved by demanding that the corrected signals in the negative incorporation events of the binary encoding list be as close to the actual background noise level as possible. Specifically, we perform perturbations of parameters $\lambda$ and $\varepsilon$ on the CAFIE matrix in the algorithm:

$$\Delta q_\lambda = [M^{-1}(p', 1-\Delta\lambda, 0)]^*q - q,$$

$$\Delta q_\varepsilon = [M^{-1}(p', 1, \Delta\varepsilon)]^*q - q, \qquad \text{Equations (11-12):}$$

where $M(p', \lambda, \varepsilon)$ is the CAFIE matrix described above, $\Delta q_\lambda$, and $\Delta q_\varepsilon$ are the changes of the flowgram in response to perturbations $\Delta\lambda$ and $\Delta\varepsilon$ with the binary encoding list p', and p is the theoretical flowgram computed by the Standard CAFIE correction.

In the recursive CAFIE method, new $\lambda$ and $\varepsilon$ are obtained by the following procedure: The perturbation increments ($t_\lambda$, $t_\varepsilon$) are computed by minimizing the following expression:

$$\arg(t_\lambda, t_\varepsilon) \sum_i |q(i) + t_\lambda \Delta q_\lambda(i) + t_\varepsilon \Delta q_\varepsilon(i) - \text{noise}|^2 \qquad \text{Equation (13)}$$

for $i$ that $p'(i) = 0$ where noise is the average of the flow signals associated with negative incorporation events (p' (i)=0) of the first 48 flows. After the values of $t_\lambda$ and $t_\varepsilon$ are determined the CAFIE correction parameters ($\lambda$, $\varepsilon$) are computed as:

$$\lambda = 1 - t_\lambda \Delta\lambda,$$

$$\varepsilon = t_\varepsilon \Delta\varepsilon. \qquad \text{Equations (14-15):}$$

In this way, the $\lambda$ and $\varepsilon$ are ensured as the optimal pair that minimizes the out-of-phase CAFIE error. Finally, the CAFIE correction is performed $$p^{(1)} = [M^{-1}(p', \varepsilon, \lambda)]^*q, \qquad \text{Equation (16):}$$

to obtain a new CAFIE-corrected theoretical flowgram $p^{(1)}$.

The above-stated procedure is repeated iteratively: at iteration n+1, the flowgram $p^{(n)}$ is used to estimate the binary encoding list $p'^{(n)}$, perform again CAFIE search by the minimization procedure (13), and obtain through the perturbation formulae (14-16) a new CAFIE-corrected flowgram $p^{(n+1)}$ and CAFIE parameters ($\varepsilon^{(n+1)}$, $\lambda^{(n+1)}$)

$$p^{(n+1)} = [M^{-1}(p'^{(n)}, \varepsilon^{(n+1)}, \lambda^{(n+1)})]^*q. \qquad \text{Equation (17):}$$

In some embodiments the recursive procedure continues until the binary encoding list converges, $p'^{(n+1)} = p'^{(n)}$. The positive flow list i, where $p'^{(n)}(i)=1$, approximates the flow positions that show positive nucleotide incorporation. The more accurately the positive flow list is estimated by the algorithm results in a more accurate correction of phasic asynchrony. Thus the recursive algorithm uses the CAFIE-corrected flowgram iteratively resulting in a recursively corrected flowgram at convergence; at each iteration the algorithm obtains a better estimation for the CAFIE parameters ($\varepsilon^{(n)}$, $\lambda^{(n)}$) and binary encoding $p'^{(n)}$ which gives more accurate CAFIE correction for the phase errors in the next iteration.

In some embodiments the recursive procedure continues until the CAFIE parameters converges, ($\varepsilon^{(n+1)}$, $\lambda^{(n+1)}$)=($\varepsilon^{(n)}$, $\lambda^{(n)}$) which also indicates convergence of the binary encoding list by the nature of how the binary encoding list is calculated using the CAFIE parameters. One advantage of using the CAFIE parameters to determine convergence is that it is computationally more efficient than estimating convergence of the binary encoding list p'.

Embodiments of the system and method for phasic synchrony flow order design and uses described herein ameliorate CAFIE error accumulation during the SBS process that result in longer high-quality read length and higher read accuracy for a sequencing run. For example, when implemented in an SBS run the phasic synchrony flow order embodiments derived by embodiments of the method allows members of a population of substantially identical template molecules that have fallen behind the correct phase of the sequencing reactions to catch up with the correct phase and re-synchronize themselves at certain positions of the flows in the phasic synchrony flow order during the sequencing run. For example, if a subset of template nucleic acid molecules from a population of substantially identical template nucleic acid molecules fails to incorporate a nucleotide species during a flow, such as a T species the result is that it falls out of phasic synchrony with the rest of the population (i.e. the subset is behind the phase of the rest of the population). If the nucleotides species is repeated in a flow soon thereafter (i.e. within 1-3 flows) there is a likelihood that the subset will incorporate the T nucleotide before the rest of the population advances in phase (i.e. by incorporation of the next complementary species) resulting a re-synchronization of the subset with the rest of the population and recovery of the phasic synchrony error.

It is important to note that embodiments of phasic synchrony flow order described herein are not restricted to 4-nucleotide cyclic orders, and can contain long flow order sequences such as 24, 32, 40 or higher number of nucleotide flow sequences in a cycle. It is also important to note that the flow order sequences can be any length and do not have to be a multiple of 4.

CAFIE Simulation and Read Length for Flow Order Design

Simulations of CAFIE error and read length for flow order design were performed that included numerically generated flow orders with k-base nucleotide sequences per flow cycle. For example, "TACG" flow order is a 4-base flow order, and "TCGTGACGTCTA" (SEQ ID NO: 1) cyclic flow is a 12-base flow order. For a given flow order and given rates of carry-forward and incomplete extension, simulations of expected flowgram signals that would be obtained using an SBS method from E. coli reference sequences were generated. The simulation included flowgrams from about 10,000 randomly selected regions from the E. coli reference sequence to mimic a shotgun sequencing of the genome. The simulated flowgrams were base-called by rounding the flowgram values to the nearest integers. No signal correction was performed on the simulated flowgrams to avoid bias of the CAFIE correction method in the signal processing.

Because of CAFIE error, flowgram signals become out of phase with errors accumulated with increased number of nucleotide flows. The initial part of the flowgram has better quality (lower error rate) than that in the latter stage of the sequencing, which usually contains ambiguous signals with a high degree of error (phase error). The read lengths in the simulation were thus truncated from the 3' end such that the "high-quality" portion of the read has less than 3% accumulated error for each read.

The high-quality read length "L" was computed by averaging the trimmed read lengths of all the 10,000 reads in the simulations. The theoretical extension rate "R" of a flow order was also calculated which is defined as the average number of complementary sequence positions to the template molecule a single nucleotide flow can extend in a perfect sequencing condition (no CAFIE). Thus, for a flow order and given CAFIE rates we arrived at a length L and an extension rate R, derived from the CAFIE modeling and simulation.

Figure 2:
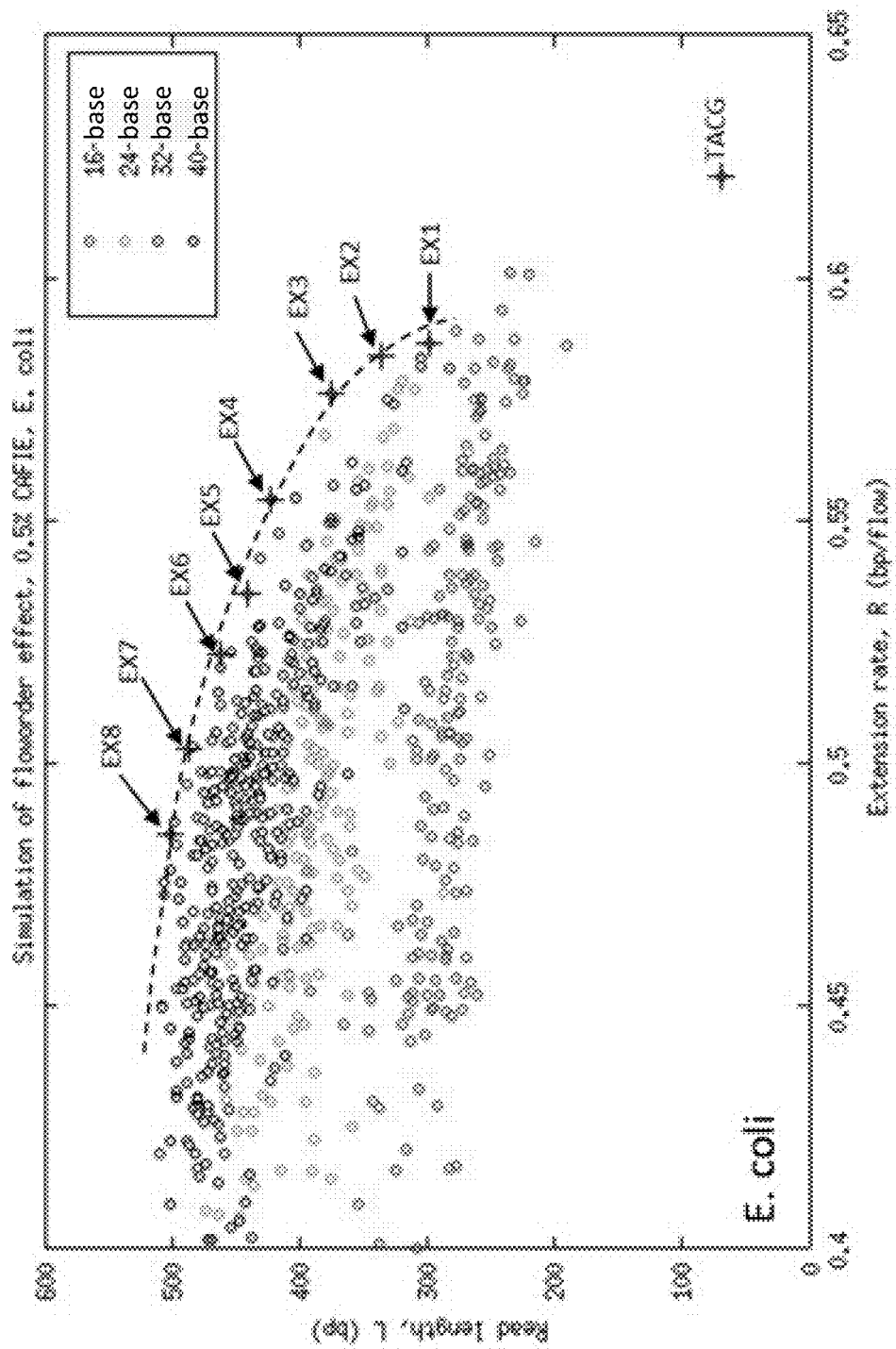
FIG. 2 is a simplified graphical representation of one embodiment of the effects of a simulated sequencing by synthesis process on an E. coli reference sequence using a plurality of computed flow orders.

The above procedure was repeated many times with various flow orders constructed by juxtaposing the 4 nucleotide species (A, T, G and C) in the flow orders. Results for these calculations are plotted in FIG. 2, showing simulated read length L vs. the extension rate R for 16, 24, 32 and 40-base flow order of nucleotide species per flow cycle, each of which contains 200 flow orders generated through a computer program. The simulations assumed 0.5% incompletion and 0.5% carry-forward rate in the sequencing by synthesis, with 1600 nucleotide flows (mimicking SBS system runs) which are cyclic repeats of the flow orders. For example, FIG. 2 provides an illustrative example of simulated read length L vs. extension rate R for randomly selected flow orders on an E. coli sequence with 0.5% CAFIE. Reads are trimmed to 3% accumulated error and simulations were performed with 1600 nucleotide flows in the sequencing by synthesis to mimic the number of nucleotide flows in an SBS system. The dashed line demarcates the border where improvement of the read length saturates. 'TACG' (cross symbol) corresponds to a flow order previously used in SBS embodiments. EX1~EX8 (crosses) are examples of flow orders located near the saturation (dashed) curve and represent effective flow orders which give long read length with the associated extension rate.

As illustrated in FIG. 2, longer read length L can be achieved by flow orders with less extension rates R, where nucleotide flow orders are designed such that out-of-phase templates in a population of substantially identical templates have a better chance to catch up and re-synchronize with the correct phase of extension of the population at certain nucleotide flows during the flow order. There is also a dependence in the number of bases in the flow order, where longer read length can be achieved with flow orders comprising a higher number of bases in the flow order for a given extension rate. However, this effect saturates at flow orders of 32~40 bases of nucleotide flows per cycle, beyond which the read length does not improve further (FIG. 2).

The result of "TACG" flow order embodiment implemented in previous SBS embodiments is also plotted in FIG. 2, as a reference. It is observed that the TACG flow order has a high extension rate R but gives very short read length L when CAFIE is 0.5%. In this case, phase error accumulates rapidly, and signal correction has to be applied numerically on the reads to correct the errors and recover the read lengths.

An "effective" flow order should give long read length and also have high extension rate. Thus, those flow orders near the saturation curve (dashed line) in FIG. 2 are examples of effective flow orders. Some of them (EX1~EX8) are marked in the figure and their nucleotide sequences are listed in Table 2 below. Among these, EX8 is close to optimum (longest read length) from the simulations with 0.5% CAFIE. It will therefore be appreciated that a flow order with a read length of greater than about 400 bp and an extension rate of equal to or less than about 0.55 bp/flow generally provides higher quality data due to lower rates of CAFIE error accumulation.

TABLE 2

Examples of effective flow orders (long read length L for the extension rate R)

| ID | Floworder | R (bp/flow) | L (bp) | SEQ ID NO: |
|---|---|---|---|---|
| TACG | TACG | 0.621 | 69 | — |
| EX1 | TACGTCTGAGCATCGATCGATGTACAGCTACG | 0.587 | 299 | 2 |
| EX2 | AGCGTACTGCATGCATCAGTATGC | 0.584 | 337 | 3 |
| EX3 | CATATGCATGATCAGCTCGATGACGCATGCTG | 0.576 | 376 | 4 |
| EX4 | TGCTCGATGATGTCATCGACTGACTGACAGCA | 0.554 | 423 | 5 |
| EX5 | ACAGCGTGATACTGTCGATGACTGCATCATCG | 0.535 | 441 | 6 |
| EX6 | ACGTGTACGACGTATCACGTATGCACTGAGTC | 0.522 | 462 | 7 |
| EX7 | ACAGTCTCGATGACAGTATACGTCTGCGATGC | 0.503 | 487 | 8 |
| EX8 | TGCTACATGATGACGCAGACTGTCATAGCTCG | 0.485 | 502 | 9 |

Note that flow order embodiments effective for reducing the accumulation of CAFIE error depends on the degree of CAFIE error (represented by the CAFIE parameters) and the sequence composition of the template nucleic acid molecule when sequencing or reference sequence when performing simulations. It will also be appreciated by those of ordinary skill in the art that the ultimate reliable read lengths may further be improved by applying the CAFIE corrections to the sequence data as described above in the post sequencing processing. The examples presented above were derived by assuming 0.5% of incompletion efficiency and 0.5% carry-forward rates, with E. coli as reference genome.

To demonstrate the effects of phasic synchrony flow order embodiments on multiple genomes having different sequence composition characteristics, the simulations were extended to include reference sequences of T. thermophilis (70% GC content) and C. jejuni (30% GC), in addition to E. coli (50% GC). They represent genomes of high-GC, low-GC and neutral GC content, respectively. Simulations were performed with the same procedure described above, but read length (L) and extension rate (R) are now averaged values of the reads randomly selected from the three reference genomes.

Figure 3:
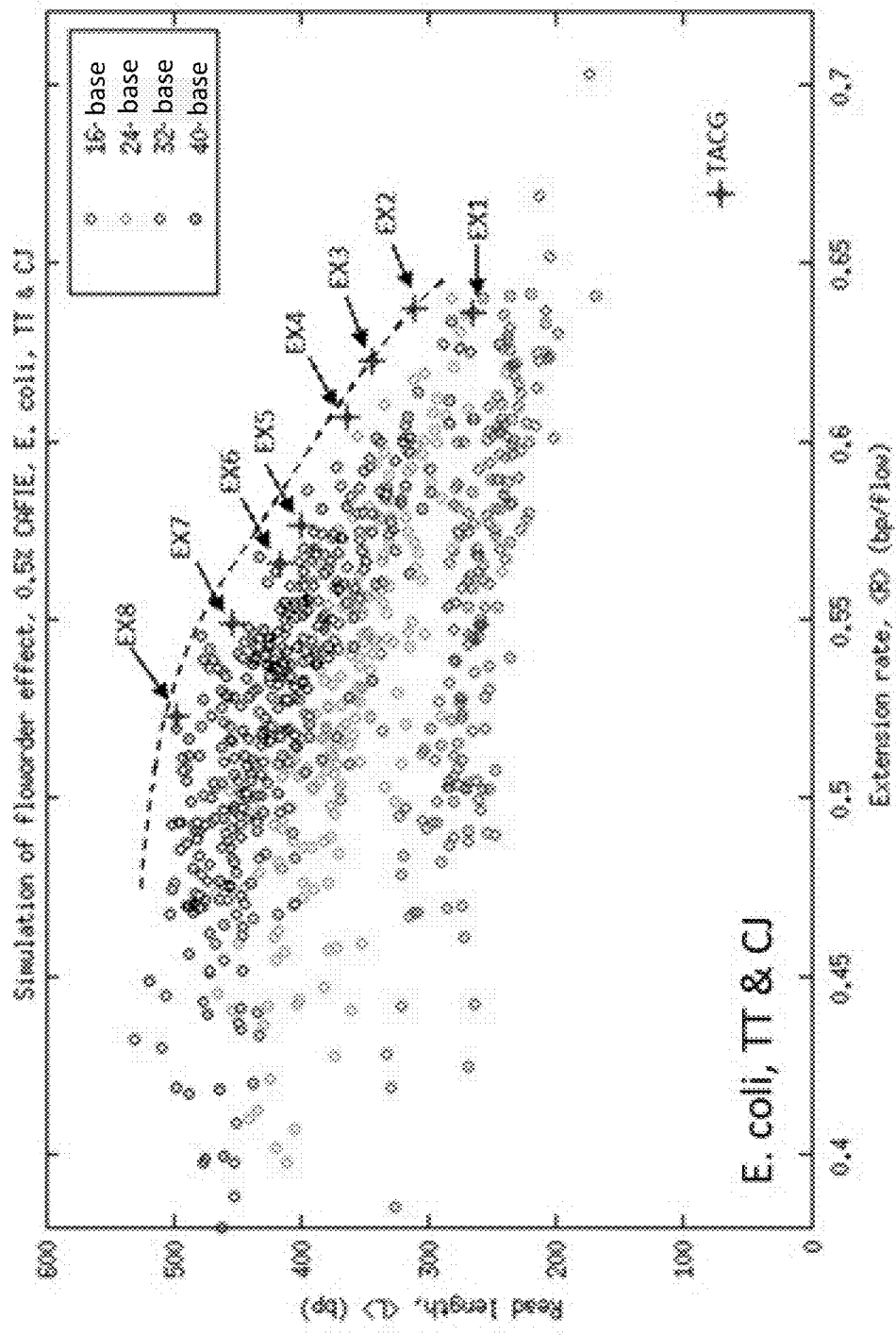
FIG. 3 is a simplified graphical representation of one embodiment of the effects of a simulated sequencing by synthesis process on an average of E. coli reference, T. thermophilus, and C. jejuni sequences using a plurality of computed flow orders.

FIG. 3 shows the simulation results, with the same flow orders EX1~EX8 (Table 2) also marked in the figure. FIG. 3 illustrates that the T. thermophilus and C. jejuni results are consistent with those derived from the simulations of E. coli case, showing longer read lengths achieved with flow orders of that have lower extension rates. Flow orders EX1~EX8 listed in table 2 remain effective and close to the saturation line (dashed line, FIG. 3) approaching maximal read length for the corresponding extension rate. For example, FIG. 3 provides an illustrative example of simulated read length L vs. extension rates R with randomly selected flow orders—average of multiple genomes including E. coli, T. thermophilus and C. jejuni, with 0.5% CAFIE. Reads were trimmed to 3% cumulated error and simulations were performed with 1600 nucleotide flows in the sequencing by synthesis to mimic the number of nucleotide flows in an SBS system. The dashed line demarcates the boarder where read length improvement saturates, 'TACG' corresponds to a flow order previously used in SBS embodiments. EX1~EX8 are the same flow orders that were obtained and shown in FIG. 2.

The simulations provided in FIGS. 2 and 3 show that, when a reference sequence is available, a set of effective flow orders can be derived from the CAFIE modeling and simulation. These flow orders can reduce phase error and result in longer high-quality read length, even without correcting phase error numerically in a signal processing. Flow orders that achieve maximal or nearly maximal read length (EX8, e.g.) can be derived from the simulation modeling, when incompletion and carry-forward rates are known or can be estimated prior to the sequencing runs. Thus, the method is especially useful for amplicon/target sequencing, where consensus sequence of the amplicon is available, and effective flow orders can be derived to tailor the nucleotide sequences of the sample.

In de-novo sequencing or applications where reference sequences are not available, a generic class of flow orders can also be derived by including multiple genomes in the simulations. These flow orders are shown to be effective, and specific examples such as EX1 to EX8 are given in Table 2. Any of these flow orders can be implemented in a sequencing script deployed for de-novo sequencing applications.

For both re-sequencing (amplicons) and de-novo sequencing applications, incompletion and carry-forward rate can be inferred from the run history for the instrument or reagent. For example, it is observed that incompletion is at 0.2%~0.5% (or 0.998~0.995 completion efficiency) and carry-forward is 0.5~1% for some embodiments of SBS platform, across many instruments and reagent lots. With this generic information of the CAFIE, optimal flow order embodiments can be obtained through the simulation modeling to give longest read length. In the present example, flow order EX8 and those near EX8 in the figures are examples when CAFIE is 0.5%.

A list of effective flow orders can also be derived a priori when simulated against the GC content of the genomes. An effective phasic synchrony flow order for a sequencing run can then be selected from the list according to the GC-content of the library sample, whose information may be attainable prior to the sequencing run.

Alternatively, an effective phasic synchrony flow order can be selected during a sequencing run after acquisition of data from a sufficient number of flows to estimate the GC content and implement the best fitting flow order for the GC content estimation. For example, a list of effective phasic synchrony flow order embodiments can be derived a priori when simulated against CAFIE, which can be estimated for a run using the flowgram signals at the beginning stage of the sequencing flows (e.g. first 40 or 80 nucleotide flows of the run) with any flow order or an embodiment of phasic synchrony flow order (e.g. EX1~8). An optimal phasic synchrony flow order can then be selected that is tailored specifically to the sequence composition (i.e. GC content) and degree of CAFIE error of the run during the run time, and be implemented for the remaining nucleotide flows in the sequencing.

In some embodiments a plurality of flow orders having different composition and/or characteristics may be employed sequentially over a number of flow cycle iterations of in a sequencing run. In some embodiments each flow order may have common characteristics with other flow orders as well as unique characteristics. It will also be appreciated that one or more of the flow orders can be repeated over a sequencing run in a random or non-random manner.

Another embodiment of a flow order optimization algorithm comprises A Monte Carlo simulation of optimizing the nucleotide flow order with respect to a reference genome. A set of reference sequence reads (e.g. 5,000 reads with 1,500 bases long) can be generated from a user-specified reference genome. (e.g. E. coli). The algorithm takes an input flow order and generates the perfect flowgrams of the reads based on the flow order. The "raw flowgrams" (i.e. flowgrams with CAFIE error) are then generated by perturbing the ideal flowgrams using a CAFIE matrix which assumes certain degrees of carry forward (e.g. 0.5%) and completion efficiency (e.g. 99.5%). To gauge the effectiveness of the flow order in reducing the out-of-phase error signals, the raw flowgrams are base called directly by rounding off the intensity values to the nearest integers. Cumulative error up to the base positions was calculated by comparing the base called sequence and the reference reads. The reads are trimmed so that the cumulative error is below a threshold value (e.g. 3%). The average read length is then calculated. The effectiveness of a flow order is measured by its theoretical efficiency $\varepsilon_T$ (average number of bases incorporated per flow without the CAFIE effect) and the observed efficiency $\varepsilon_O$ (average number of bases incorporated per flow with the CAFIE effect). In general, the higher the theoretical efficiency, the lower the observed efficiency as the CAFIE error would build up faster. A quality score can be constructed to measure the effectiveness of the flow order, e.g.

$$Q = w_1 \varepsilon_T + w_2 \varepsilon_O,$$

where $w_1$ and $w_2$ are the weights given to the respective efficiencies, e.g. 0.5 and 0.5.

A new flow order is generated by permuting a random pair of nucleotide species in the flow order. The generation of the flowgrams, the base calling and the trimming are repeated. The quality score Q' of the new flow order is then calculated. If Q' is larger than Q, the new flow order is accepted. If Q' is smaller than Q, the new flow order is accept with the probability.

$$P = \exp[(Q'-Q)/T]$$

where T is the "temperature" which controls the chance of a suboptimal flow order to be accepted. The whole process is repeated until the quality score is maximized and an optimal flow order, with respect to the reference genome and the chosen parameters $w_1$, $w_2$ and T, was obtained.

If T is very large, all flow orders with lower quality scores would be accepted. Conversely if T is very small, no permutations that resulted in a lower quality score would be accepted. A typical value of T can be estimated by calculating the quantity Q'–Q of various permutations. T can be chosen such that about half of the moves are accepted for negative values of Q'–Q.

The parameter T can be gradually changing, for example from a high to a lower value, over the course of simulation. This method, known as simulated annealing, can help narrow down the search within the neighborhood of the optimal region.

The completion efficiency can be gradually changing, for example form a high to a low value, from the beginning to the end of the flowgram in order to model the change in the enzymatic efficiency throughout a sequencing run. The carry forward parameter can be treated in a similar way.

The model can extend to optimizing multiple reference genomes. There would be a quality score Qi for each reference genome. A total quality score calculated from the combination of these individual quality scores can be used. In particular, a weight-average quality score of these individual quality scores can be used.

EXAMPLES

Comparison of Sequencing Data, TACG and Flow Orders EX1, & EX3

Flow orders EX1, and EX3 (Table 2) were tested in SBS instruments using standard reagent kits and materials. Their read lengths are summarized in the Table 3 below, showing the results of (a) without CAFIE correction in the signal processing (to avoid bias of CAFIE correction) and (b) results of full signal processing with CAFIE correction.

In the tested flow orders the average read lengths were >400 bp even without CAFIE correction (bold texts in the table). As a comparison, SBS runs with the TACG flow order had read lengths 100~200 bp when without CAFIE correction of the sequence data. Results after full signal processing were also greatly improved; see Table 4 for the mapping statistics. Thus improvement from the effective flow order embodiments is consistent.

TABLE 3

| SBS with Phasic Synchrony flow orders, E. coli | | | | |
|---|---|---|---|---|
| | | | E. coli, read length (bp) | |
| Run ID | Floworder | Region | (a) no Cafie crr. | (b) w/ Cafie crr. |
| 1 | EX1 | 3 | 362 | 779 |
| 1 | EX1 | 6 | 352 | 775 |
| 2 | EX1 | 3 | 334 | 724 |
| 2 | EX1 | 6 | 225 | 728 |
| 3 | EX1 | 3 | 416 | 804 |
| 5 | EX3 | 2 | 519 | 714 |
| 5 | EX3 | 6 | 528 | 728 |
| 5 | EX3 | 5 | 532 | 745 |
| 6 | EX1 | 2 | 556 | 820 |
| 6 | EX1 | 6 | 560 | 813 |
| SBS with Phasic Synchrony flow orders, TT | | | | |
| | | | T. thermophilus, read length (bp) | |
| Run ID | Floworder | Region | (a) no Cafie crr. | (b) w/ Cafie crr. |
| 1 | EX1 | 2 | 284 | 635 |
| 1 | EX1 | 7 | 275 | 628 |
| 2 | EX1 | 2 | 276 | 540 |

TABLE 3-continued

| | | | | |
|---|---|---|---|---|
| 2 | EX1 | 7 | 263 | 539 |
| 3 | EX1 | 2 | 314 | 693 |
| 3 | EX1 | 6 | 254 | 519 |
| 3 | EX1 | 7 | 259 | 540 |
| 5 | EX3 | 4 | 360 | 552 |
| 5 | EX3 | 7 | 340 | 486 |
| 6 | EX1 | 7 | 367 | 635 |

SBS with Phasic Synchrony flow orders, CJ

| | | *C. jejuni*, read length (bp) | |
|---|---|---|---|
| Run ID | Floworder | Region | (a) no Cafie crr. | (b) w/ Cafie crr. |
| 5 | EX3 | 3 | 387 | 757 |
| 5 | EX3 | 8 | 401 | 760 |
| 6 | EX1 | 3 | 465 | 838 |
| 6 | EX1 | 8 | 476 | 844 |

TABLE 4

SBS with TACG flow orders, *E. coli*

| | | *E. coli* | |
|---|---|---|---|
| Run ID | Floworder | Region | (a) no Cafie crr. | (b) w/ Cafie crr. |
| 7 | TACG | 3 | 168 | 616 |
| 7 | TACG | 5 | 170 | 631 |
| 7 | TACG | 7 | 164 | 578 |
| 8 | TACG | 3 | 148 | 620 |
| 8 | TACG | 5 | 164 | 644 |
| 8 | TACG | 8 | 156 | 572 |
| 9 | TACG | 2 | 214 | 694 |
| 9 | TACG | 6 | 204 | 692 |
| 9 | TACG | 5 | 192 | 707 |

TABLE 4-continued

SBS with TACG flow orders, TT

| | | *T. thermophilus* | |
|---|---|---|---|
| Run ID | Floworder | Region | (a) no Cafie crr. | (b) w/ Cafie crr. |
| 7 | TACG | 2 | 130 | 373 |
| 7 | TACG | 4 | 127 | 361 |
| 7 | TACG | 6 | 135 | 433 |
| 8 | TACG | 4 | 120 | 370 |
| 8 | TACG | 6 | 132 | 436 |
| 8 | TACG | 7 | 126 | 402 |
| 9 | TACG | 4 | 143 | 533 |
| 9 | TACG | 7 | 168 | 511 |

SBS with TACG flow orders, CJ

| | | *C. jejuni* | |
|---|---|---|---|
| Run ID | Floworder | Region | (a) no Cafie crr. | (b) w/ Cafie crr. |
| 9 | TACG | 3 | 159 | 682 |
| 9 | TACG | 8 | 150 | 678 |

Comparison of Sequencing Data—Mapping to Reference Genome

Figure 4A:
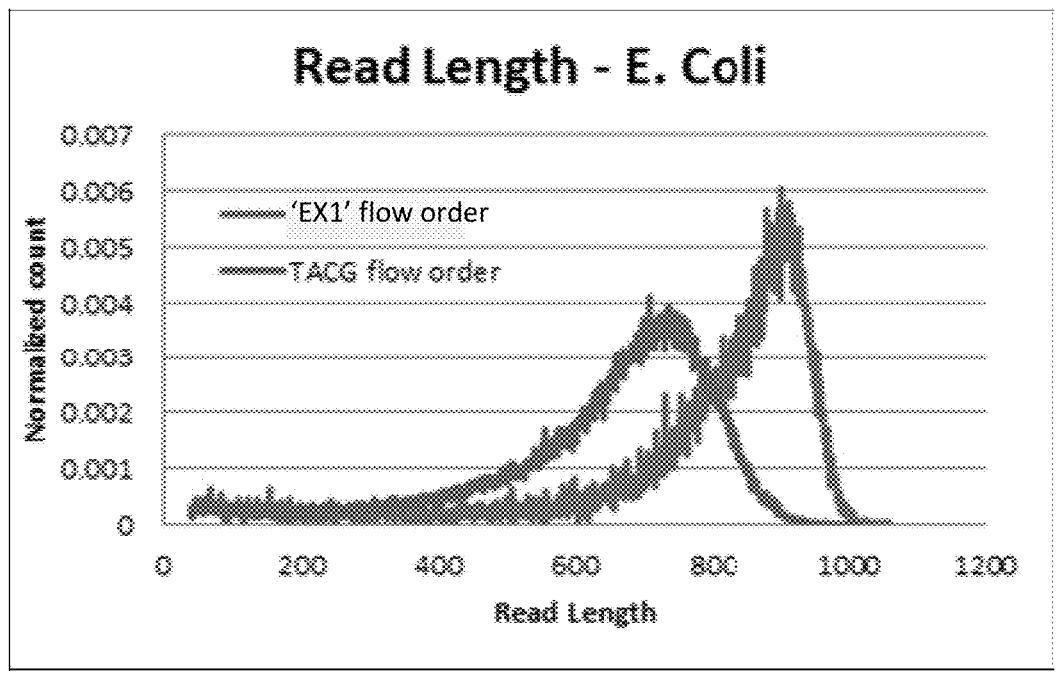
FIGS. 4A and 4B are simplified graphical representations of one embodiment of a comparison of mapped length histogram and error at base positions for runs with flow orders 'EX1' and 'TACG'.
Figure 4B:
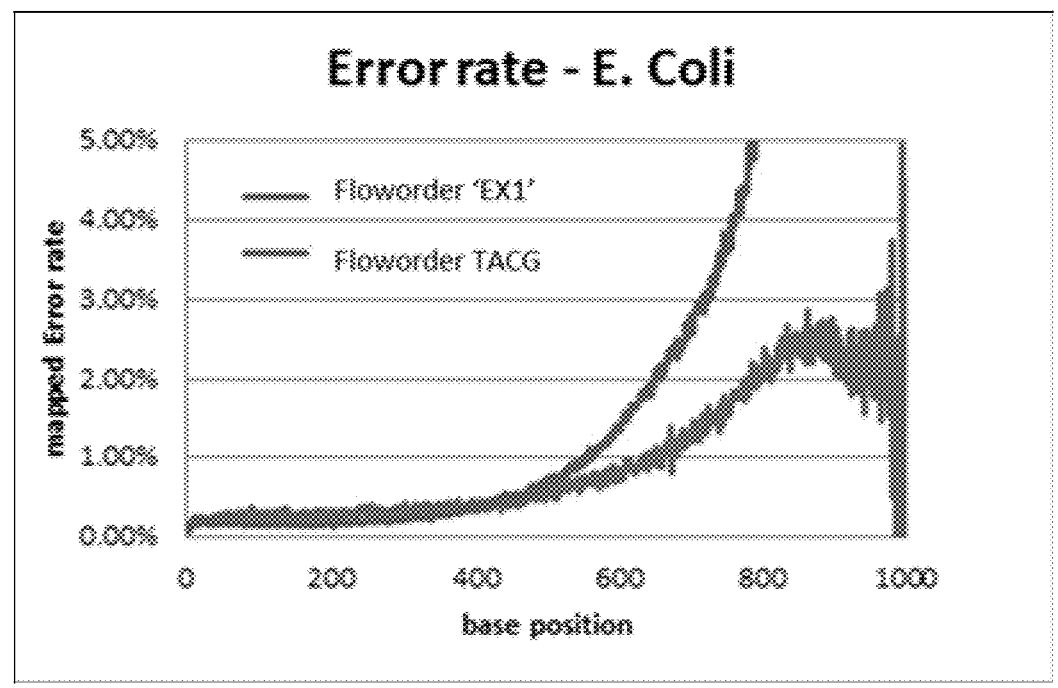

Mapping results to the reference sequences of the genomes are summarized in Table 5 below, showing the results of 3 sequencing runs with floworder EX1 (Table 2). For *E. coli* the mapped lengths were all above 700 bp and for *T. thermophilus* the read lengths were variable but all still above 500 bp (the variability seemed to be library sample dependent). The run data were processed with data analysis software with the full processing including CAFIE correction. The results showed that more than 100 bp longer mapped lengths were obtained with EX1 compared to those runs done using TACG flow order. A comparison of the mapped length histogram and read error rate at the base position are shown in FIG. 4.

TABLE 5

Sequencing results for three test runs on SBS instruments with flow order 'EX1'

*E. coli*

| | Run ID (region) | | | | |
|---|---|---|---|---|---|
| | Run 1 (reg 3) | Run 1 (reg 6) | Run 2 (reg 3) | Run 2 (reg 6) | Run 3 (reg 3) |
| Mapped Reads | 104,616 | 90,231 | 44,046 | 47,706 | 116,827 |
| Mapped Bases | 81,719,915 | 69,688,005 | 31,915,462 | 34,578,064 | 93,965,723 |
| Cumul. Err 500B | 0.29% | 0.31% | 0.74% | 0.93% | 0.23% |
| Err at 500B | 0.45% | 0.48% | 0.45% | 0.58% | 0.34% |
| Inf Read Error | 0.54% | 0.60% | 0.74% | 1.01% | 0.45% |
| Last 100 Base IRE | 1.68% | 1.97% | 1.21% | 2.06% | 1.39% |
| Avg. Map Length | 781 | 772 | 724 | 724 | 804 |
| 7mer Accuracy | 78.48% | 75.66% | 77.30% | 71.11% | 79.55% |

*T. thermophilus*

| | Run ID (region) | | | | | | |
|---|---|---|---|---|---|---|---|
| | Run 1 (reg 2) | Run 1 (reg 7) | Run 2 (reg 2) | Run 2 (reg 7) | Run 3 (reg 2) | Run 3 (reg 6) | Run 3 (reg 7) |
| Mapped Reads | 124,241 | 121,900 | 47,831 | 38,197 | 119,307 | 114,405 | 108,356 |
| Mapped Bases | 78,819,271 | 76,545,982 | 25,830,815 | 20,569,127 | 81,798,891 | 58,936,924 | 57,130,942 |
| Cumul. Err 500B | 0.51% | 0.54% | 0.95% | 0.97% | 0.44% | 0.68% | 0.58% |
| Err at 500B | 0.96% | 0.93% | 0.99% | 1.03% | 0.90% | 1.19% | 1.14% |
| Inf Read Error | 0.81% | 0.82% | 1.02% | 1.04% | 0.87% | 0.92% | 0.80% |
| Last 100 Base IRE | 2.05% | 2.01% | 1.48% | 1.49% | 2.38% | 2.35% | 2.18% |
| Avg. Map Length | 634 | 627 | 540 | 538 | 685 | 515 | 527 |
| 7mer Accuracy | 75.98% | 75.03% | 71.13% | 70.52% | 77.85% | 67.74% | 71.81% |

Other Phasic Synchrony Flow Order Embodiments
Flow Order A:

```
TACGTACGTACG (12)                        (SEQ ID NO: 10)
AGCGTACTGCATGCATCAGTATGCG (25)           (SEQ ID NO: 11)
AGCGTACTGCATGCATCAGTATGCT                (SEQ ID NO: 12)
AGCGTACTGCATGCATCAGTATCGC                (SEQ ID NO: 13)
AGCGTACTGCATGCATCAGTATGAC                (SEQ ID NO: 14)
AGCGTACTGCATGCATCAGTATCGC                (SEQ ID NO: 15)
AGCGTACTGCATGCATCAGTATGCT                (SEQ ID NO: 16)
AGCGTACTGCATGCATCAGTATGCG                (SEQ ID NO: 17)
AGCGTACTGCATGCATCAGTATGAC                (SEQ ID NO: 18)
AGCGTACTGCATGCATCAGTATCGC                (SEQ ID NO: 19)
AGCGTACTGCATGCATCAGTATGCT                (SEQ ID NO: 20)
AGCGTACTGCATGCATCAGTATGCG                (SEQ ID NO: 21)
AGCGTACTGCATGCATCAGTATGAC                (SEQ ID NO: 22)
AGCGTACTGCATGCATCAGTATGCG                (SEQ ID NO: 23)
AGCGTACTGCATGCATCAGTATGCT                (SEQ ID NO: 24)
AGCGTACTGCATGCATCAGTATCGC                (SEQ ID NO: 25)
AGCGTACTGCATGCATCAGTATGAC                (SEQ ID NO: 26)
AGCGTACTGCATGCATCAGTATGCG                (SEQ ID NO: 27)
AGCGTACTGCATGCATCAGTATCGC                (SEQ ID NO: 28)
AGCGTACTGCATGCATCAGTATGCT                (SEQ ID NO: 29)
AGCGTACTGCATGCATCAGTATGAC                (SEQ ID NO: 30)
AGCGTACTGCATGCATCAGTATGCT                (SEQ ID NO: 31)
AGCGTACTGCATGCATCAGTATCGC                (SEQ ID NO: 32)
AGCGTACTGCATGCATCAGTATGCG                (SEQ ID NO: 33)
AGCGTACTGCATGCATCAGTATGAC                (SEQ ID NO: 34)
AGCGTACTGCATGCATCAGTATCGC                (SEQ ID NO: 35)
AGCGTACTGCATGCATCAGTATGCG                (SEQ ID NO: 36)
AGCGTACTGCATGCATCAGTATGAC                (SEQ ID NO: 37)
AGCGTACTGCATGCATCAGTATGCT                (SEQ ID NO: 38)
AGCGTACTGCATGCATCAGTATGCG                (SEQ ID NO: 39)
AGCGTACTGCATGCATCAGTATCGC                (SEQ ID NO: 40)
AGCGTACTGCATGCATCAGTATGAC                (SEQ ID NO: 41)
AGCGTACTGCATGCATCAGTATGCT                (SEQ ID NO: 42)
AGCGTACTGCATGCATCAGTATGCG                (SEQ ID NO: 43)
AGCGTACTGCATGCATCAGTATGCT                (SEQ ID NO: 44)
AGCGTACTGCATGCATCAGTATGAC                (SEQ ID NO: 45)
AGCGTACTGCATGCATCAGTATCGC                (SEQ ID NO: 46)
AGCGTACTGCATGCATCAGTATGAC                (SEQ ID NO: 47)
AGCGTACTGCATGCATCAGTATCGC                (SEQ ID NO: 48)
AGCGTACTGCATGCATCAGTATGCG                (SEQ ID NO: 49)
AGCGTACTGCATGCATCAGTATGCT                (SEQ ID NO: 50)
AGCGTACTGCATGCATCAGTATGCG                (SEQ ID NO: 51)
AGCGTACTGCATGCATCAGTATGCT                (SEQ ID NO: 52)
AGCGTACTGCATGCATCAGTATGAC                (SEQ ID NO: 53)
AGCGTACTGCATGCATCAGTATCGC                (SEQ ID NO: 54)
AGCGTACTGCATGCATCAGTATGCT                (SEQ ID NO: 55)
AGCGTACTGCATGCATCAGTATGCG                (SEQ ID NO: 56)
AGCGTACTGCATGCATCAGTATGAC                (SEQ ID NO: 57)
AGCGTACTGCATGCATCAGTATCGC                (SEQ ID NO: 58)
                          -continued
AGCGTACTGCATGCATCAGTATGAC                (SEQ ID NO: 59)
AGCGTACTGCATGCATCAGTATGCG                (SEQ ID NO: 60)
AGCGTACTGCATGCATCAGTATCGC                (SEQ ID NO: 61)
AGCGTACTGCATGCATCAGTATGCT                (SEQ ID NO: 62)
AGCGTACTGCATGCATCAGTATGCG                (SEQ ID NO: 63)
AGCGTACTGCATGCATCAGTATGAC                (SEQ ID NO: 64)
AGCGTACTGCATGCATCAGTATCGC                (SEQ ID NO: 65)
AGCGTACTGCATGCATCAGTATGCT                (SEQ ID NO: 66)
AGCGTACTGCATGCATCAGTATGAC                (SEQ ID NO: 67)
AGCGTACTGCATGCATCAGTATGCT                (SEQ ID NO: 68)
AGCGTACTGCATGCATCAGTATCGC                (SEQ ID NO: 69)
AGCGTACTGCATGCATCAGTATGCG                (SEQ ID NO: 70)
AGCGTACTGCATGCATCAGTATGCT                (SEQ ID NO: 71)
AGCGTACTGCATGCATCAGTATCGC                (SEQ ID NO: 72)
AGCGTACTGCATGCATCAGTATGCG                (SEQ ID NO: 73)
AGCGTACTGCATGCATCAGTATGAC                (SEQ ID NO: 74)
AGCGTACTGCATGCATCAGTATGCG                (SEQ ID NO: 75)
AGCGTACTGCATGCATCAGTATGAC                (SEQ ID NO: 76)
AGCGTACTGCATGCATCAGTATCGC                (SEQ ID NO: 77)
AGCGTACTGCATGCATCAGTATGCT                (SEQ ID NO: 78)
AGCGTACTGCATGCATCAGTATGAC                (SEQ ID NO: 79)
AGCGTACTGCATGCATCAGTATGCG                (SEQ ID NO: 80)
AGCGTACTGCATGCATCAGTATCGC                (SEQ ID NO: 81)
AGCGTACTGCATGCATCAGTATGCT                (SEQ ID NO: 82)
AGCGTACTGCATGCATCAGTATGCG                (SEQ ID NO: 83)
AGCGTACTGCATGCATCAGTATGCT                (SEQ ID NO: 84)
AGCGTACTGCATGCATCAGTATGAC                (SEQ ID NO: 85)
AGCGTACTGCATGCATCAGTATCGC                (SEQ ID NO: 86)
AGCGTACTGCATGCATCAGTATGCT                (SEQ ID NO: 87)
AGCGTACTGCATGCATCAGTATGAC                (SEQ ID NO: 88)
AGCGTACTGCATGCATCAGTATGCG                (SEQ ID NO: 89)
AGCGTACTGCATGCATCAGTATCGC                (SEQ ID NO: 90)
```

Flow Order A Characteristics:

Due to repeated sequence composition in combination with three variable positions in the last three positions that occur every 25 flows after first 12 flows (4 base flow order cycled 3 times), the complete order is interpreted as a cyclically repeating 25 flow, flow order with a variable component.

Repeat Region
A=6; G=5; C=5; T=6
First variable position=G, or C
Second variable position=A, G, or C
Third variable position=T, G, or C
Combination of First–Third variable positions=at least one G and one C 3 iterations 4 base flow order; 80 iterations Repeat/variable regions of 25 flows; 2012 Total Flows Flow Order B:

```
TACGTACGTACG (12)
(SEQ ID NO: 91)

ATGTAGTCGAGCATCATCTGACGCAGTACGTGC (33 Total; T = 8; A = 8; C = 8; G = 9)
(SEQ ID NO: 92)

ATGATCTCAGTCAGCAGCTATGTCAGTGCATGC (33 Total; T = 9; A = 8; C = 8; G = 8)
(SEQ ID NO: 93)

AGTGACTGATCGTCATCAGCTAGCATCGACTGC (33 Total; T = 8; A = 8; C = 9; G = 8)
(SEQ ID NO: 94)

ATAGATCGCATGACGATCGCATATCGTCAGTGC (33 Total; T = 8; A = 9; C = 8; G = 9)
(SEQ ID NO: 95)

ATGTAGTCGAGCATCATCTGACGCAGTACGTGC (33 Total; T = 8; A = 8; C = 8; G = 9)
(SEQ ID NO: 96)

ATGATCTCAGTCAGCAGCTATGTCAGTGCATGC (33 Total; T = 9; A = 8; C = 8; G = 8)
(SEQ ID NO: 97)

ATAGATCGCATGACGATCGCATATCGTCAGTGC (33 Total; T = 8; A = 9; C = 8; G = 8)
(SEQ ID NO: 98)
```

```
AGTGACTGATCGTCATCAGCTAGCATCGACTGC  (33 Total; T = 8; A = 8; C = 9; G = 8)
(SEQ ID NO: 99)

ATGTAGTCGAGCATCATCTGACGCAGTACGTGC  (33 Total; T = 8; A = 8; C = 8; G = 9)
(SEQ ID NO: 100)

ATAGATCGCATGACGATCGCATATCGTCAGTGC  (33 Total; T = 8; A = 9; C = 8; G = 8)
(SEQ ID NO: 101)

ATGATCTCAGTCAGCAGCTATGTCAGTGCATGC  (33 Total; T = 9; A = 8; C = 8; G = 8)
(SEQ ID NO: 102)

AGTGACTGATCGTCATCAGCTAGCATCGACTGC  (33 Total; T = 8; A = 8; C = 9; G = 8)
(SEQ ID NO: 103)

ATGTAGTCGAGCATCATCTGACGCAGTACGTGC  (33 Total; T = 8; A = 8; C = 8; G = 9)
(SEQ ID NO: 104)

AGTGACTGATCGTCATCAGCTAGCATCGACTGC  (33 Total; T = 8; A = 8; C = 9; G = 8)
(SEQ ID NO: 105)

ATAGATCGCATGACGATCGCATATCGTCAGTGC  (33 Total; T = 8; A = 9; C = 8; G = 8)
(SEQ ID NO: 106)

ATGATCTCAGTCAGCAGCTATGTCAGTGCATGC  (33 Total; T = 9; A = 8; C = 8; G = 8)
(SEQ ID NO: 107)

ATGTAGTCGAGCATCATCTGACGCAGTACGTGC  (33 Total; T = 8; A = 8; C = 8; G = 9)
(SEQ ID NO: 108)

ATAGATCGCATGACGATCGCATATCGTCAGTGC  (33 Total; T = 8; A = 9; C = 8; G = 8)
(SEQ ID NO: 109)

AGTGACTGATCGTCATCAGCTAGCATCGACTGC  (33 Total; T = 8; A = 8; C = 9; G = 8)
(SEQ ID NO: 110)

ATGATCTCAGTCAGCAGCTATGTCAGTGCATGC  (33 Total; T = 9; A = 8; C = 8; G = 8)
(SEQ ID NO: 111)

AGTGACTGATCGTCATCAGCTAGCATCGACTGC
(SEQ ID NO: 112)

ATAGATCGCATGACGATCGCATATCGTCAGTGC
(SEQ ID NO: 113)

ATGATCTCAGTCAGCAGCTATGTCAGTGCATGC
(SEQ ID NO: 114)

ATGTAGTCGAGCATCATCTGACGCAGTACGTGC
(SEQ ID NO: 115)

ATAGATCGCATGACGATCGCATATCGTCAGTGC
(SEQ ID NO: 116)

ATGATCTCAGTCAGCAGCTATGTCAGTGCATGC
(SEQ ID NO: 117)

AGTGACTGATCGTCATCAGCTAGCATCGACTGC
(SEQ ID NO: 118)

ATGTAGTCGAGCATCATCTGACGCAGTACGTGC
(SEQ ID NO: 119)

ATGATCTCAGTCAGCAGCTATGTCAGTGCATGC
(SEQ ID NO: 120)

ATAGATCGCATGACGATCGCATATCGTCAGTGC
(SEQ ID NO: 121)

ATGTAGTCGAGCATCATCTGACGCAGTACGTGC
(SEQ ID NO: 122)

AGTGACTGATCGTCATCAGCTAGCATCGACTGC
(SEQ ID NO: 123)

ATAGATCGCATGACGATCGCATATCGTCAGTGC
(SEQ ID NO: 124)

ATGTAGTCGAGCATCATCTGACGCAGTACGTGC
(SEQ ID NO: 125)
```

```
ATGATCTCAGTCAGCAGCTATGTCAGTGCATGC
(SEQ ID NO: 126)

AGTGACTGATCGTCATCAGCTAGCATCGACTGC
(SEQ ID NO: 127)

ATGATCTCAGTCAGCAGCTATGTCAGTGCATGC
(SEQ ID NO: 128)

AGTGACTGATCGTCATCAGCTAGCATCGACTGC
(SEQ ID NO: 129)

ATAGATCGCATGACGATCGCATATCGTCAGTGC
(SEQ ID NO: 130)

ATGTAGTCGAGCATCATCTGACGCAGTACGTGC
(SEQ ID NO: 131)

ATGATCTCAGTCAGCAGCTATGTCAGTGCATGC
(SEQ ID NO: 132)

ATGTAGTCGAGCATCATCTGACGCAGTACGTGC
(SEQ ID NO: 133)

AGTGACTGATCGTCATCAGCTAGCATCGACTGC
(SEQ ID NO: 134)

ATAGATCGCATGACGATCGCATATCGTCAGTGC
(SEQ ID NO: 135)

AGTGACTGATCGTCATCAGCTAGCATCGACTGC
(SEQ ID NO: 136)

ATGTAGTCGAGCATCATCTGACGCAGTACGTGC
(SEQ ID NO: 137)

ATAGATCGCATGACGATCGCATATCGTCAGTGC
(SEQ ID NO: 138)

ATGATCTCAGTCAGCAGCTATGTCAGTGCATGC
(SEQ ID NO: 139)

AGTGACTGATCGTCATCAGCTAGCATCGACTGC
(SEQ ID NO: 140)

ATGTAGTCGAGCATCATCTGACGCAGTACGTGC
(SEQ ID NO: 141)

ATGATCTCAGTCAGCAGCTATGTCAGTGCATGC
(SEQ ID NO: 142)

ATAGATCGCATGACGATCGCATATCGTCAGTGC
(SEQ ID NO: 143)

AGTGACTGATCGTCATCAGCTAGCATCGACTGC
(SEQ ID NO: 144)

ATGATCTCAGTCAGCAGCTATGTCAGTGCATGC
(SEQ ID NO: 145)

ATAGATCGCATGACGATCGCATATCGTCAGTGC
(SEQ ID NO: 146)

ATGTAGTCGAGCATCATCTGACGCAGTACGTGC
(SEQ ID NO: 147)
```

Flow Order B Characteristics:

Due to repeated sequence composition of the first position and last three positions in combination with a 29 flow variable region that occur every 33 flows after first 12 flows (4 base flow order cycled 3 times), the complete order is interpreted as a cyclically repeating 33 flow, flow order with a substantial variable component.

First Position=Always A

Variable Region 29 positions=Always has one species that has 8 flows with the rest 7 (not including repeated positions which increase flow number of all species by 1)

Last Three positions=Always TCG

Combination of first and second repeat regions=each nucleotide species represented once 3 iterations 4 base flow order; 55 iterations Repeat/variable regions of 33 flows; 1827 Total Flows Having described various embodiments and implementations, it should be apparent to those skilled in the relevant art that the foregoing is illustrative only and not limiting, having been presented by way of example only. Many other schemes for distributing functions among the various functional elements of the illustrated embodiments are possible. The functions of any element may be carried out in various ways in alternative embodiments.

What is claimed is:

1. A method for sequencing a nucleic acid template using a flow order that minimizes the accumulation of phasic synchrony error in sequence data, comprising the steps of:
   (a) introducing a numerically generated sequential ordering of nucleotide species comprising a k-base length into a sequencing by synthesis reaction environment, wherein the numerically generated sequential ordering of nucleotide species comprises a predetermined series of flows of nucleotide species that is generated by
      (i) simulating expected flowgram signals that would be generated using a sequencing by synthesis method to acquire sequence data from one or more known reference sequences, wherein the sequence data comprises an accumulation of phasic synchrony error from the one or more known reference sequences and
      (ii) selecting the series of flows of nucleotide species that demonstrates a high read length characteristic and a low extension rate characteristic for the one or more known reference sequences, wherein the high read length characteristic is greater than about 400 bp and the low extension rate characteristic is less than or equal to 0.55 bp/flow;
   (b) acquiring signals from the sequencing by synthesis reaction environment in response to incorporation of the nucleotide species in an extension reaction of one or more populations of substantially identical nucleic acid template molecules, wherein the signals comprise a measure of error from a subset of nucleic acid template molecules from one or more of the populations fall behind a phase of extension; and
   (c) cyclically repeating the introduction of the numerically generated sequential ordering of nucleotide species and acquisition of signals for a number of iterations, wherein the subset of nucleic acid molecules re-synchronize with the phase of extension that reduces the measure of error due to the high read length characteristic and the low extension rate characteristic of the sequential ordering.

2. The method of claim 1, wherein:
the sequencing by synthesis reaction environment comprises an array of wells.

3. The method of claim 1, wherein:
the k-base length is selected from the group consisting of 16, 24, 32, and 40 base lengths.

4. The method of claim 1, wherein:
the k-base length comprises a length in a range of 32-40 bases.

5. The method of claim 1, wherein:
the read length characteristic comprises a measure of read length that comprises less than 3% of the accumulated phasic synchrony error.

6. The method of claim 1, wherein:
the extension rate characteristic comprises an average number of complementary sequence positions to the template molecule a single nucleotide flow can extend.

7. The method of claim 1, wherein:
the read length characteristic is greater than about 400 bp and the extension rate characteristic is less than or equal to about 0.55 bp/flow at a 0.5% incompletion rate and a 0.5% carry-forward rate.

* * * * *